US009657283B2

(12) United States Patent
Yaver et al.

(10) Patent No.: US 9,657,283 B2
(45) Date of Patent: May 23, 2017

(54) POLYPEPTIDES HAVING XYLANASE ACTIVITY AND POLYNUCLEOTIDES THEREOF

(71) Applicant: Novozymes, Inc., Davis, CA (US)

(72) Inventors: Debbie Yaver, Davis, CA (US); Paul Harris, Carnation, WA (US); Suzanne Otani, Elk Grove, CA (US); Janine Lin, Davis, CA (US); Hanshu Ding, Davis, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 14/668,599

(22) Filed: Mar. 25, 2015

(65) Prior Publication Data

US 2015/0197737 A1 Jul. 16, 2015

Related U.S. Application Data

(62) Division of application No. 13/151,128, filed on Jun. 1, 2011, now Pat. No. 8,999,694, which is a division of application No. 11/054,191, filed on Feb. 9, 2005, now Pat. No. 7,960,160.

(60) Provisional application No. 60/544,461, filed on Feb. 12, 2004, provisional application No. 60/544,429, filed on Feb. 12, 2004, provisional application No. 60/544,431, filed on Feb. 12, 2004.

(51) Int. Cl.
*C12N 15/56* (2006.01)
*C12N 9/24* (2006.01)

(52) U.S. Cl.
CPC ........... *C12N 9/2482* (2013.01); *C12N 9/248* (2013.01); *C12Y 302/01008* (2013.01)

(58) Field of Classification Search
CPC ..... C12N 9/248; C12N 9/2482; C12N 9/2485
See application file for complete search history.

(56) References Cited

U.S. PATENT DOCUMENTS 7,504,490 B1 3/2009 Weinstock et al.

FOREIGN PATENT DOCUMENTS

| | | |
|---|---|---|
| EP | 0 468 596 | 7/1991 |
| EP | 0463706 B1 | 7/1991 |
| WO | 91/19782 | 12/1991 |
| WO | 92/01793 | 2/1992 |
| WO | 92/17573 | 10/1992 |
| WO | 02/24926 | 3/2002 |
| WO | 03/012071 | 2/2003 |

OTHER PUBLICATIONS

Bailey et al, 1989, Appl Microbiol Biotechnol 30, 5-10.
Balajee et al, 2006, Euk Cell 5(10), 1705-1712.
Cerro e Silva et al, 1999, Revista De Microbiol 30, 114-119.
Fedorova et al, 2008, Genetics 4(4), 1-13.
Grajek, 1987, Biotechnol Lett 9(5), 353-356.
Guo et al, 2004, PNAS 101(25), 9205-9210.
Hill et al, 1998, Biochem Biophys Res Comm 244, 573-577.
Lenartovicz et al, 2002, J Basic Microbiol 42(6), 388-39.
Nierman et al, 2005, Nature 438, 1151-1156.
Samson et al, 2007, Studies in Mycology 59, 147-203.
Yoder et al, 1986, Am Phytopathol Soc 76(4), 383-385.
Beg et al, 2001, Appl Microbiol Biotechnol 56(3-4), 326-338.
Detroym R. W. In: Organic Chemicals from Biomass, (CRC Press, Boca Raton, Fla, 1981) 19-41.
Paice and Jurasek, J. Wood Chem. Technol. 4: 187-198, 1984.
Pommier and Fuentes, 1989, Tappi Journal 187-191.
Senior et al., 1988, Biotechnol. Letters 10: 907-9121.
Shei et al., 1985, Biotech. and Bioeng. vol. XXVII, pp. 533-538.
Fournier et al., 1985, Biotech. and Bioeng. vol. XXVII, pp. 539-546.

*Primary Examiner* — Rebecca Prouty
(74) *Attorney, Agent, or Firm* — Robert Starnes

(57) ABSTRACT

The present invention relates to isolated polypeptides having xylanase activity and isolated polynucleotides encoding the polypeptides. The invention also relates to nucleic acid constructs, vectors, and host cells comprising the polynucleotides as well as methods for producing and using the polypeptides.

30 Claims, 14 Drawing Sheets

```
      M  R  F   S  L  A  A   T  A  L   L  A  G   L  A  T  A   A  P  S   S  N  K
  1  ATGCGTTTCT CCCTTGCCGC CACCGCTCTT CTCGCTGGCC TGGCCACGGC AGCGCCTTCG AGCAACAAGA
     N  N  V  N   L  D  K   L  A  R   R  N  G  M   L  W  F   G  T  A   A  D  I  P
 71  ACAACGTCAA TCTTGATAAG CTTGCTCGGC GTAATGGCAT GCTTTGGTTC GGCACTGCAG CCGATATCCC
       G  T  S   E  T  T   D  K  P  Y   L  S  I   L  R  K   Q  F  G  E   M  T  P
141  TGGTACCTCA GAAACAACCG ACAAGCCTTA TCTGAGCATC CTGCGCAAGC AGTTCGGCGA AATGACACCC
      A  N  A   L  K  V  S   Q  S  D
211  GCAAACGCAT TGAAGGTGAG CCAGAGTGAT AGTACACCTC ATCTCGTGTC GGCGCTGACC AGACGATGTT
                 F  M  Y   T  E  P  E   Q  N  V   F  N  F   T  Q  G  D   Y  F  M
281  ATTCACATAG TTCATGTATA CCGAGCCCGA GCAGAATGTC TTCAACTTCA CTCAAGGGGA CTACTTCATG
      D  L  A   D  H  Y  G   H  A  V   R  C  H   N  L  V  W   A  S  Q   V  S  D
351  GACTTGGCCG ATCACTATGG TCACGCCGTG CGCTGCCATA ACCTCGTCTG GGCCAGCCAA GTGTCCGACT
     W  V  T  S   R  N  W   T  A  T   E  L  K  E   V  M  K   N  H  I   F  K  T  V
421  GGGTCACCTC CAGGAACTGG ACCGCCACAG AACTCAAAGA AGTGATGAAG AACCACATAT TCAAGACCGT
       Q  H  F   G  K  R   C  Y  A  W   D  V  V   N  E  A   I  N  G  D   G  T  F
491  CCAACATTTT GGCAAGCGCT GCTACGCGTG GGACGTCGTC AATGAAGCTA TTAATGGGGA CGGGACCTTT
      S  S  S   V  W  Y  D   T  I  G   E  E  Y   F  Y  L  A   F  Q  Y   A  Q  E
561  TCCTCCAGTG TGTGGTACGA CACAATTGGC GAGGAATACT TCTACCTTGC ATTCCAGTAT GCCCAGGAAG
     A  L  A  Q   I  H  A   N  Q  V   K  L  Y  Y   N  D  Y   G  I  E   N  P  G  P
631  CCCTGGCGCA GATTCACGCC AACCAGGTCA AGCTTTACTA TAACGACTAT GGCATTGAGA ACCCCGGCCC
       K  A  D   A  V  L   K  L  V  A   E  L  R   K  R  G   I  R  I  D   G  V  G
701  CAAGGCAGAT GCTGTTCTGA AGCTAGTCGC CGAGTTGCGG AAGCGGGGCA TTCGCATTGA CGGAGTCGGT
      L  E  S   H  F  I  V   G  E  T   P  S  L   A  D  Q  L   A  T  K   K  A  Y
771  CTCGAGTCCC ACTTCATCGT CGGCGAGACT CCTTCGCTGG CTGACCAGCT CGCCACCAAG AAGGCTTATA
     I  E  A  G   L  E  V   A  I  T   E  L  D  V   R  F  S   Q  A  P   F  Y  T  A
841  TCGAGGCCGG ACTTGAGGTC GCCATCACCG AACTTGACGT CCGCTTTTCT CAGGCCCCGT TCTACACCGC
       E  A  Q   K  Q  Q   A  A  D  Y   Y  A  S   V  A  S   C  K  H  A   G  P  R
```

Fig. 1A

```
 911 CGAGGCCCAA AAGCAGCAGG CTGCCGACTA CTATGCTAGC GTCGCCAGTT GCAAGCATGC CGGACCGCGC
       C  V  G   V  V  V  W   D  F  D   D  A  Y   S  W  I  P   G  T  F   E  G  Q
 981 TGTGTTGGTG TTGTAGTCTG GGATTTCGAT GACGCCTACT CGTGGATTCC GGGTACCTTC GAGGGACAGG
     G  G  A  C   L  Y  N   E  T  L   E  V  K  P   A  F  Y   A  A  A   E  A  L  E
1051 GTGGCGCCTG TCTATATAAT GAGACACTCG AGGTGAAGCC GGCCTTCTAT GCTGCTGCCG AGGCGTTGGA
       N  K  P   C  T  V   C  *
1121 GAACAAGCCC TGCACTGTAT GCTAG
```

Fig. 1B

```
        M  V  V   L  S  K  L   V  S  S   I  L  F   V  S  L  V   S  A  G   V  I  D
  1  ATGGTCGTCC TCAGCAAGCT CGTCAGCAGC ATTCTCTTTG TCTCCCTGGT TTCGGCGGGC GTGATCGACG
     E  R  Q  A   A  G  I   N  Q  A   F  T  S  H   G  K  K   Y  F  G   T  A  S  D
 71  AACGCCAGGC AGCCGGCATC AACCAGGCGT TTACCTCCCA TGGCAAGAAG TACTTTGGCA CCGCCAGTGA
       Q  A  L   L  Q  K   S  Q  N  E   A  I  V   R  K  D   F  G  Q  L   T  P  E
141  CCAAGCTCTG CTCCAGAAGT CGCAGAATGA GGCCATTGTG CGCAAAGACT TTGGCCAGCT GACGCCGGAG
      N  S  M   K  W  D  A   T  E
211  AATAGCATGA AGTGGGATGC GACTGAGCGT AGGTCTCTCG GCCACTGTGG CTGACGTTAA CTTGTTGACA
                    A  S   Q  G  R   F  N  F  A   G  A  D   F  L
281  TGACTGTCTG TGTAGCATCG CAAGGAAGAT TCAACTTCGC TGGTGCTGAT TTCCTGGTAT GCAATCTGCT
                                          V   N  Y  A   K  Q  N  G   K  K  V
351  CATCTCGGTC GAGCTCCTGC TGAAGGACAA TAAATAGGTC AACTATGCAA AACAGAATGG CAAGAAGGTC
      R  G  H   T  L
421  CGCGGACACA CCTTAGGTAT TCATGCGCCC TCACGGCATT TCGAGGATAC AGCCAAGCTG ACAGTGTAGT
       W  H  S   Q  L  P   S  W  V  S   A  I  S   D  K  N   T  L  T  S   V  L  K
491  CTGGCACTCC CAACTCCCGT CCTGGGTGTC GGCTATCAGC GACAAAAACA CCCTGACCTC GGTGCTGAAG
      N  H  I   T  T  V  M   T  R  Y   K  G  Q   I  Y  A  W
561  AACCACATCA CCACCGTCAT GACCCGGTAC AAGGGCCAGA TCTACGCCTG GGTATTTTGC CCTCTATCCC
                                      D  V   V  N  E  I   F  N  E   D  G  S
631  ACACAATGCC AGCCCCAGCT AATAGCTGCA AAGGACGTCG TCAACGAGAT CTTCAACGAG GACGGCTCCC
     L  R  D  S   V  F  S   R  V  L   G  E  D  F   V  R  I   A  F  E   T  A  R  S
701  TCCGCGACAG CGTCTTCTCC CGCGTGCTGG GCGAGGACTT TGTGCGGATT GCCTTCGAGA CGGCGCGCTC
       V  D  P   S  A  K   L  Y  I  N   D  Y  K
771  TGTGGATCCC TCGGCGAAGC TGTACATCAA CGATTACAAG TAAGCTTGTG GTTTTGTCGA GAGATGTACT
                                L  D   S  A  S   Y  G  K   T  Q  G  M   V  R  Y
841  CCGTCCTGGA TCTGACCATC ACAGTCTCGA CTCGGCTAGC TATGGCAAAA CCCAGGGGAT GGTGAGATAT
      V  K  K   W  L  A  A   G  I  P   I  D  G   I  G
911  GTCAAGAAGT GGCTGGCTGC GGGCATTCCT ATCGATGGAA TCGGTGAGCA CAGGTCGCGG AGCTGTGTGT
                                      Q  T   H  L  G  A   G  A  S   S  S  V
```

Fig. 7A

```
 981  GATGATTGTA CGCTGACTCT TCCTGAAGGC ACTCAAACCC ACCTTGGTGC GGGTGCTTCG TCCAGCGTCA

      K  G                                                    A  L    T  A  L
1051  AAGGATAAGT CTCCTTGGTT TTCTTGCCTA CGTAACGCTG ACCCCCCGTG TACAGCATTG ACTGCTCTTG
      A  S  S  G   V  S  E   V  A  I   T  E  L  D   I  A  G   A  S  S   Q  D  Y  V
1121  CGTCTTCCGG CGTCTCTGAG GTCGCCATTA CCGAGCTGGA TATCGCGGGT GCGAGCTCCC AGGACTACGT
        N                                                     V  V    K  A  C
1191  CAATGTATGT CTCCTGATTG CCAGTGGCAG GGTCATCGAT ACTAATAGAA ACAGGTCGTC AAGGCATGCC
      L  D  V  P   K  C  V   G  I  T   V  W  G  V   S  D  R   D  S  W   R  S  G  S
1261  TGGATGTCCC CAAGTGTGTG GGAATCACCG TCTGGGGGGT GTCGGACAGG GACTCGTGGC GCTCCGGCTC
        S  P  L   L  F  D   S  N  Y  Q   P  K  A   A  Y  N   A  I  I  A   A  L  *
1331  GTCTCCGCTG CTGTTCGACA GCAACTACCA GCCCAAGGCG GCGTATAATG CCATCATTGC TGCTCTCTGA
```

Fig. 7B

```
       M  V  H   L  S  S  L   A  A  A   L  A  A   L  P  L
    1 ATGGTCCATC TATCTTCATT GGCAGCAGCC CTGGCTGCTC TGCCTCTGTA TGTTTACCCA CTCACGAGAG
                                    V   Y  G  A   G  L  N  T   A  A  K   A  K  G
   71 GAGGAACAGC TTTGACATTG CTATAGTGTA TATGGAGCTG GCCTGAACAC AGCAGCCAAA GCCAAAGGAC
      L  K  Y  F   G  S  A   T  D  N   P  E  L  T   D  S  A   Y  V  A   Q  L  S  N
  141 TAAAGTACTT TGGTTCCGCC ACGGACAATC CAGAGCTCAC GGACTCTGCG TATGTCGCGC AACTGAGCAA
        T  D  D   F  G  Q   I  T  P  G   N  S  M   K
  211 CACCGATGAT TTTGGTCAAA TCACACCCGG AAACTCCATG AAGGTTTGCT TACGTCTGCC TCCCTGGAGC
                                                W   D  A  T   E  P  S   Q  N  S  F
  281 ATTGCCTCAA AAGCTAATTG GTTGTTTTGT TTGGATAGTG GGATGCCACC GAGCCTTCTC AGAATTCTTT
        S  F  A   N  G  D   A  V  V  N   L  A  N   K  N  G   Q  L  M  R   C  H  T
  351 TTCGTTCGCA AATGGAGACG CCGTGGTCAA TCTGGCGAAC AAGAATGGCC AGCTGATGCG ATGCCATACT
       L  V  W   H  S  Q  L   P  N  W
  421 CTGGTCTGGC ACAGTCAGCT ACCGAACTGG GGTATGTAAA CGTCTTGTCT ATTCTCAAAT ACTCTCTAAC
               V   S  S  G   S  W  T   N  A  T  L   L  A  A   M  K  N   H  I  T  N
  491 AGTTGACAGT CTCTAGCGGG TCATGGACCA ATGCGACCCT TTTGGCGGCC ATGAAGAATC ATATCACCAA
        V  V  T   H  Y  K   G  K  C  Y   A  W  D   V  V  N   E
  561 TGTGGTTACT CACTACAAGG GGAAGTGCTA CGCCTGGGAT GTTGTCAATG AAGGTTTGTT GCTCCATCTA
                                                    A  L  N   E  D  G   T  F  R  N
  631 TCCTCAATAG TTCTTTTGAA ACTGACAAGC CTGTCAATCT AGCCCTGAAC GAGGACGGTA CTTTCCGTAA
        S  V  F   Y  Q  I   I  G  P  A   Y  I  P   I  A  F   A  T  A  A   A  A  D
  701 CTCTGTCTTC TACCAGATCA TCGGCCCAGC ATACATTCCT ATTGCGTTCG CCACGGCTGC TGCCGCAGAT
       P  D  V   K  L  Y  Y   N  D  Y   N  I  E   Y  S  G  A   K  A  T   A  A  Q
  771 CCCGACGTGA AACTCTACTA CAACGACTAC AACATTGAAT ACTCAGGCGC CAAAGCGACT GCTGCGCAGA
      N  I  V  K   M  I  K   A  Y  G   A  K  I  D   G  V  G   L  Q  A   H  F  I  V
  841 ATATCGTCAA GATGATCAAG GCCTACGGCG CGAAGATCGA CGGCGTCGGC CTCCAGGCAC ACTTTATCGT
        G  S  T   P  S  Q   S  D  L  T   T  V  L   K  G  Y   T  A  L  G   V  E  V
  911 CGGCAGCACT CCGAGTCAAT CGGATCTGAC GACCGTCTTG AAGGGCTACA CTGCTCTCGG CGTTGAGGTG
       A  Y  T   E  L  D  I   R  M  Q   L  P  S   T  A  A  K   L  A  Q   Q  S  T
  981 GCCTATACCG AACTTGACAT CCGCATGCAG CTGCCCTCGA CCGCCGCAAA GCTGGCCCAG CAGTCCACTG
      D  F  Q  G   V  A  A   A  C  V   S  T  T  G   C  V  G   V  T  I   W  D  W  T
```

Fig. 9A

```
1051  ACTTCCAAGG CGTGGCCGCA GCATGCGTTA GCACCACTGG CTGCGTGGGT GTCACTATCT GGGACTGGAC
         D  K  Y   S  W  V   P  S  V  F   Q  G  Y   G  A  P   L  P  W  D   E  N  Y
1121  CGACAAGTAC TCCTGGGTCC CCAGCGTGTT CCAAGGCTAC GGCGCCCCAT TGCCTTGGGA TGAGAACTAT
        V  K  K   P  A  Y  D   G  L  M   A  G  L   G  A  S  G   S  G  T   T  T  T
1191  GTGAAGAAGC CAGCGTACGA TGGCCTGATG GCGGGTCTTG GAGCAAGCGG CTCCGGCACC ACAACGACCA
      T  T  T  T   S  T  T   T  G  G   T  D  P  T   G  V  A   Q  K  W   G  Q  C  G
1261  CTACTACTAC TTCTACTACG ACAGGAGGTA CGGACCCTAC TGGAGTCGCT CAGAAATGGG GACAGTGTGG
         G  I  G   W  T  G   P  T  T  C   V  S  G   T  T  C   Q  K  L  N   D  W  Y
1331  CGGTATTGGC TGGACCGGGC CAACAACTTG TGTCAGTGGT ACCACTTGCC AAAAGCTGAA TGACTGGTAC
        S  Q  C   L  *
1401  TCACAGTGCC TGTAA
```

Fig. 9B

SEQUENCE LISTING

```
<160> NUMBER OF SEQ ID NOS: 25

<210> SEQ ID NO 1
<211> LENGTH: 1145
<212> TYPE: DNA
<213> ORGANISM: Aspergillus fumigatus

<400> SEQUENCE: 1

atgcgtttct cccttgccgc caccgctctt ctcgctggcc tggccacggc agcgccttcg     60

agcaacaaga acaacgtcaa tcttgataag cttgctcggc gtaatggcat gctttggttc    120

ggcactgcag ccgatatccc tggtacctca gaaacaaccg acaagcctta tctgagcatc    180

ctgcgcaagc agttcggcga aatgacaccc gcaaacgcat tgaaggtgag ccagagtgat    240

agtacacctc atctcgtgtc ggcgctgacc agacgatgtt attcacatag ttcatgtata    300

ccgagcccga gcagaatgtc ttcaacttca ctcaagggga ctacttcatg gacttggccg    360

atcactatgg tcacgccgtg cgctgccata acctcgtctg ggccagccaa gtgtccgact    420

gggtcacctc caggaactgg accgccacag aactcaaaga agtgatgaag aaccacatat    480

tcaagaccgt ccaacatttt ggcaagcgct gctacgcgtg ggacgtcgtc aatgaagcta    540

ttaatgggga cgggaccttt tcctccagtg tgtggtacga cacaattggc gaggaatact    600

tctaccttgc attccagtat gcccaggaag ccctggcgca gattcacgcc aaccaggtca    660

agctttacta taacgactat ggcattgaga accccggccc caaggcagat gctgttctga    720

agctagtcgc cgagttgcgg aagcggggca ttcgcattga cggagtcggt ctcgagtccc    780

acttcatcgt cggcgagact ccttcgctgg ctgaccagct cgccaccaag aaggcttata    840

tcgaggccgg acttgaggtc gccatcaccg aacttgacgt ccgcttttct caggccccgt    900

tctacaccgc cgaggcccaa aagcagcagg ctgccgacta ctatgctagc gtcgccagtt    960

gcaagcatgc cggaccgcgc tgtgttggtg ttgtagtctg ggatttcgat gacgcctact   1020

cgtggattcc gggtaccttc gagggacagg gtggcgcctg tctatataat gagacactcg   1080

aggtgaagcc ggccttctat gctgctgccg aggcgttgga gaacaagccc tgcactgtat   1140

gctag                                                                1145


<210> SEQ ID NO 2
<211> LENGTH: 364
<212> TYPE: PRT
<213> ORGANISM: Aspergillus fumigatus

<400> SEQUENCE: 2

Met Arg Phe Ser Leu Ala Ala Thr Ala Leu Leu Ala Gly Leu Ala Thr
1               5                   10                  15

Ala Ala Pro Ser Ser Asn Lys Asn Asn Val Asn Leu Asp Lys Leu Ala
            20                  25                  30

Arg Arg Asn Gly Met Leu Trp Phe Gly Thr Ala Ala Asp Ile Pro Gly
        35                  40                  45
```

-continued

```
Thr Ser Glu Thr Thr Asp Lys Pro Tyr Leu Ser Ile Leu Arg Lys Gln
    50                  55                  60

Phe Gly Glu Met Thr Pro Ala Asn Ala Leu Lys Val Ser Gln Ser Asp
65                  70                  75                  80

Phe Met Tyr Thr Glu Pro Glu Gln Asn Val Phe Asn Phe Thr Gln Gly
                85                  90                  95

Asp Tyr Phe Met Asp Leu Ala Asp His Tyr Gly His Ala Val Arg Cys
            100                 105                 110

His Asn Leu Val Trp Ala Ser Gln Val Ser Asp Trp Val Thr Ser Arg
        115                 120                 125

Asn Trp Thr Ala Thr Glu Leu Lys Glu Val Met Lys Asn His Ile Phe
    130                 135                 140

Lys Thr Val Gln His Phe Gly Lys Arg Cys Tyr Ala Trp Asp Val Val
145                 150                 155                 160

Asn Glu Ala Ile Asn Gly Asp Gly Thr Phe Ser Ser Ser Val Trp Tyr
                165                 170                 175

Asp Thr Ile Gly Glu Glu Tyr Phe Tyr Leu Ala Phe Gln Tyr Ala Gln
            180                 185                 190

Glu Ala Leu Ala Gln Ile His Ala Asn Gln Val Lys Leu Tyr Tyr Asn
        195                 200                 205

Asp Tyr Gly Ile Glu Asn Pro Gly Pro Lys Ala Asp Ala Val Leu Lys
    210                 215                 220

Leu Val Ala Glu Leu Arg Lys Arg Gly Ile Arg Ile Asp Gly Val Gly
225                 230                 235                 240

Leu Glu Ser His Phe Ile Val Gly Glu Thr Pro Ser Leu Ala Asp Gln
                245                 250                 255

Leu Ala Thr Lys Lys Ala Tyr Ile Glu Ala Gly Leu Glu Val Ala Ile
            260                 265                 270

Thr Glu Leu Asp Val Arg Phe Ser Gln Ala Pro Phe Tyr Thr Ala Glu
        275                 280                 285

Ala Gln Lys Gln Gln Ala Ala Asp Tyr Tyr Ala Ser Val Ala Ser Cys
    290                 295                 300

Lys His Ala Gly Pro Arg Cys Val Gly Val Val Val Trp Asp Phe Asp
305                 310                 315                 320

Asp Ala Tyr Ser Trp Ile Pro Gly Thr Phe Glu Gly Gln Gly Gly Ala
                325                 330                 335

Cys Leu Tyr Asn Glu Thr Leu Glu Val Lys Pro Ala Phe Tyr Ala Ala
            340                 345                 350

Ala Glu Ala Leu Glu Asn Lys Pro Cys Thr Val Cys
        355                 360


<210> SEQ ID NO 3
<211> LENGTH: 1400
<212> TYPE: DNA
<213> ORGANISM: Aspergillus fumigatus

<400> SEQUENCE: 3

atggtcgtcc tcagcaagct cgtcagcagc attctctttg tctccctggt ttcggcgggc      60

gtgatcgacg aacgccaggc agccggcatc aaccaggcgt ttacctccca tggcaagaag     120

tactttggca ccgccagtga ccaagctctg ctccagaagt cgcagaatga ggccattgtg     180

cgcaaagact ttggccagct gacgccggag aatagcatga agtgggatgc gactgagcgt     240

aggtctctcg gccactgtgg ctgacgttaa cttgttgaca tgactgtctg tgtagcatcg     300

caaggaagat tcaacttcgc tggtgctgat ttcctggtat gcaatctgct catctcggtc     360
```

-continued gagctcctgc tgaaggacaa taaataggtc aactatgcaa aacagaatgg caagaaggtc 420
cgcggacaca ccttaggtat tcatgcgccc tcacggcatt tcgaggatac agccaagctg 480
acagtgtagt ctggcactcc caactcccgt cctgggtgtc ggctatcagc gacaaaaaca 540
ccctgacctc ggtgctgaag aaccacatca ccaccgtcat gacccggtac aagggccaga 600
tctacgcctg ggtattttgc cctctatccc acacaatgcc agccccagct aatagctgca 660
aaggacgtcg tcaacgagat cttcaacgag gacggctccc tccgcgacag cgtcttctcc 720
cgcgtgctgg gcgaggactt tgtgcggatt gccttcgaga cggcgcgctc tgtggatccc 780
tcggcgaagc tgtacatcaa cgattacaag taagcttgtg gttttgtcga gagatgtact 840
ccgtcctgga tctgaccatc acagtctcga ctcggctagc tatggcaaaa cccaggggat 900
ggtgagatat gtcaagaagt ggctggctgc gggcattcct atcgatggaa tcggtgagca 960
caggtcgcgg agctgtgtgt gatgattgta cgctgactct tcctgaaggc actcaaaccc 1020
accttggtgc gggtgcttcg tccagcgtca aaggataagt ctccttggtt ttcttgccta 1080
cgtaacgctg acccccgtg tacagcattg actgctcttg cgtcttccgg cgtctctgag 1140
gtcgccatta ccgagctgga tatcgcgggt gcgagctccc aggactacgt caatgtatgt 1200
ctcctgattg ccagtggcag ggtcatcgat actaatagaa acaggtcgtc aaggcatgcc 1260
tggatgtccc caagtgtgtg ggaatcaccg tctgggggt gtcggacagg gactcgtggc 1320
gctccggctc gtctccgctg ctgttcgaca gcaactacca gcccaaggcg gcgtataatg 1380
ccatcattgc tgctctctga 1400

<210> SEQ ID NO 4
<211> LENGTH: 323
<212> TYPE: PRT
<213> ORGANISM: Aspergillus fumigatus

<400> SEQUENCE: 4

Met Val Val Leu Ser Lys Leu Val Ser Ser Ile Leu Phe Val Ser Leu
1 5 10 15

Val Ser Ala Gly Val Ile Asp Glu Arg Gln Ala Ala Gly Ile Asn Gln
20 25 30

Ala Phe Thr Ser His Gly Lys Lys Tyr Phe Gly Thr Ala Ser Asp Gln
35 40 45

Ala Leu Leu Gln Lys Ser Gln Asn Glu Ala Ile Val Arg Lys Asp Phe
50 55 60

Gly Gln Leu Thr Pro Glu Asn Ser Met Lys Trp Asp Ala Thr Glu Ala
65 70 75 80

Ser Gln Gly Arg Phe Asn Phe Ala Gly Ala Asp Phe Leu Val Asn Tyr
85 90 95

Ala Lys Gln Asn Gly Lys Lys Val Arg Gly His Thr Leu Trp His Ser
100 105 110

Gln Leu Pro Ser Trp Val Ser Ala Ile Ser Asp Lys Asn Thr Leu Thr
115 120 125

Ser Val Leu Lys Asn His Ile Thr Thr Val Met Thr Arg Tyr Lys Gly
130 135 140

Gln Ile Tyr Ala Trp Asp Val Val Asn Glu Ile Phe Asn Glu Asp Gly
145 150 155 160

Ser Leu Arg Asp Ser Val Phe Ser Arg Val Leu Gly Glu Asp Phe Val
165 170 175

Arg Ile Ala Phe Glu Thr Ala Arg Ser Val Asp Pro Ser Ala Lys Leu 180 185 190

Tyr Ile Asn Asp Tyr Lys Leu Asp Ser Ala Ser Tyr Gly Lys Thr Gln
195 200 205

Gly Met Val Arg Tyr Val Lys Lys Trp Leu Ala Ala Gly Ile Pro Ile
210 215 220

Asp Gly Ile Gly Gln Thr His Leu Gly Ala Gly Ala Ser Ser Ser Val
225 230 235 240

Lys Gly Ala Leu Thr Ala Leu Ala Ser Ser Gly Val Ser Glu Val Ala
245 250 255

Ile Thr Glu Leu Asp Ile Ala Gly Ala Ser Ser Gln Asp Tyr Val Asn
260 265 270

Val Val Lys Ala Cys Leu Asp Val Pro Lys Cys Val Gly Ile Thr Val
275 280 285

Trp Gly Val Ser Asp Arg Asp Ser Trp Arg Ser Gly Ser Ser Pro Leu
290 295 300

Leu Phe Asp Ser Asn Tyr Gln Pro Lys Ala Ala Tyr Asn Ala Ile Ile
305 310 315 320

Ala Ala Leu

<210> SEQ ID NO 5
<211> LENGTH: 1415
<212> TYPE: DNA
<213> ORGANISM: Aspergillus fumigatus

<400> SEQUENCE: 5
atggtccatc tatcttcatt ggcagcagcc ctggctgctc tgcctctgta tgtttaccca 60
ctcacgagag gaggaacagc tttgacattg ctatagtgta tatggagctg gcctgaacac 120
agcagccaaa gccaaaggac taaagtactt tggttccgcc acggacaatc cagagctcac 180
ggactctgcg tatgtcgcgc aactgagcaa caccgatgat tttggtcaaa tcacacccgg 240
aaactccatg aaggtttgct tacgtctgcc tccctggagc attgcctcaa aagctaattg 300
gttgttttgt ttggatagtg ggatgccacc gagccttctc agaattcttt ttcgttcgca 360
aatggagacg ccgtggtcaa tctggcgaac aagaatggcc agctgatgcg atgccatact 420
ctggtctggc acagtcagct accgaactgg ggtatgtaaa cgtcttgtct attctcaaat 480
actctctaac agttgacagt ctctagcggg tcatggacca atgcgaccct tttggcggcc 540
atgaagaatc atatcaccaa tgtggttact cactacaagg ggaagtgcta cgcctgggat 600
gttgtcaatg aaggtttgtt gctccatcta tcctcaatag ttcttttgaa actgacaagc 660
ctgtcaatct agccctgaac gaggacggta ctttccgtaa ctctgtcttc taccagatca 720
tcggcccagc atacattcct attgcgttcg ccacggctgc tgccgcagat cccgacgtga 780
aactctacta caacgactac aacattgaat actcaggcgc caaagcgact gctgcgcaga 840
atatcgtcaa gatgatcaag gcctacggcg cgaagatcga cggcgtcggc ctccaggcac 900
actttatcgt cggcagcact ccgagtcaat cggatctgac gaccgtcttg aagggctaca 960
ctgctctcgg cgttgaggtg gcctataccg aacttgacat ccgcatgcag ctgccctcga 1020
ccgccgcaaa gctggcccag cagtccactg acttccaagg cgtggccgca gcatgcgtta 1080
gcaccactgg ctgcgtgggt gtcactatct gggactggac cgacaagtac tcctgggtcc 1140
ccagcgtgtt ccaaggctac ggcgccccat tgccttggga tgagaactat gtgaagaagc 1200
cagcgtacga tggcctgatg gcgggtcttg gagcaagcgg ctccggcacc acaacgacca 1260
ctactactac ttctactacg acaggaggta cggaccctac tggagtcgct cagaaatggg 1320
gacagtgtgg cggtattggc tggaccgggc caacaacttg tgtcagtggt accacttgcc 1380
aaaagctgaa tgactggtac tcacagtgcc tgtaa 1415

<210> SEQ ID NO 6
<211> LENGTH: 397
<212> TYPE: PRT
<213> ORGANISM: Aspergillus fumigatus

<400> SEQUENCE: 6

Met Val His Leu Ser Ser Leu Ala Ala Ala Leu Ala Ala Leu Pro Leu
1 5 10 15

Val Tyr Gly Ala Gly Leu Asn Thr Ala Ala Lys Ala Lys Gly Leu Lys
20 25 30

Tyr Phe Gly Ser Ala Thr Asp Asn Pro Glu Leu Thr Asp Ser Ala Tyr
35 40 45

Val Ala Gln Leu Ser Asn Thr Asp Asp Phe Gly Gln Ile Thr Pro Gly
50 55 60

Asn Ser Met Lys Trp Asp Ala Thr Glu Pro Ser Gln Asn Ser Phe Ser
65 70 75 80

Phe Ala Asn Gly Asp Ala Val Val Asn Leu Ala Asn Lys Asn Gly Gln
85 90 95

Leu Met Arg Cys His Thr Leu Val Trp His Ser Gln Leu Pro Asn Trp
100 105 110

Val Ser Ser Gly Ser Trp Thr Asn Ala Thr Leu Leu Ala Ala Met Lys
115 120 125

Asn His Ile Thr Asn Val Val Thr His Tyr Lys Gly Lys Cys Tyr Ala
130 135 140

Trp Asp Val Val Asn Glu Ala Leu Asn Glu Asp Gly Thr Phe Arg Asn
145 150 155 160

Ser Val Phe Tyr Gln Ile Ile Gly Pro Ala Tyr Ile Pro Ile Ala Phe
165 170 175

Ala Thr Ala Ala Ala Ala Asp Pro Asp Val Lys Leu Tyr Tyr Asn Asp
180 185 190

Tyr Asn Ile Glu Tyr Ser Gly Ala Lys Ala Thr Ala Ala Gln Asn Ile
195 200 205

Val Lys Met Ile Lys Ala Tyr Gly Ala Lys Ile Asp Gly Val Gly Leu
210 215 220

Gln Ala His Phe Ile Val Gly Ser Thr Pro Ser Gln Ser Asp Leu Thr
225 230 235 240

Thr Val Leu Lys Gly Tyr Thr Ala Leu Gly Val Glu Val Ala Tyr Thr
245 250 255

Glu Leu Asp Ile Arg Met Gln Leu Pro Ser Thr Ala Ala Lys Leu Ala
260 265 270

Gln Gln Ser Thr Asp Phe Gln Gly Val Ala Ala Ala Cys Val Ser Thr
275 280 285

Thr Gly Cys Val Gly Val Thr Ile Trp Asp Trp Thr Asp Lys Tyr Ser
290 295 300

Trp Val Pro Ser Val Phe Gln Gly Tyr Gly Ala Pro Leu Pro Trp Asp
305 310 315 320

Glu Asn Tyr Val Lys Lys Pro Ala Tyr Asp Gly Leu Met Ala Gly Leu
325 330 335

Gly Ala Ser Gly Ser Gly Thr Thr Thr Thr Thr Thr Thr Thr Ser Thr
340 345 350

-continued

Thr Thr Gly Gly Thr Asp Pro Thr Gly Val Ala Gln Lys Trp Gly Gln
        355                 360                 365

Cys Gly Gly Ile Gly Trp Thr Gly Pro Thr Thr Cys Val Ser Gly Thr
    370                 375                 380

Thr Cys Gln Lys Leu Asn Asp Trp Tyr Ser Gln Cys Leu
385                 390                 395

<210> SEQ ID NO 7
<211> LENGTH: 22
<212> TYPE: DNA
<213> ORGANISM: Aspergillus niger

<400> SEQUENCE: 7
gtgccccatg atacgcctcc gg 22

<210> SEQ ID NO 8
<211> LENGTH: 26
<212> TYPE: DNA
<213> ORGANISM: Aspergillus niger

<400> SEQUENCE: 8
gagtcgtatt tccaaggctc ctgacc 26

<210> SEQ ID NO 9
<211> LENGTH: 24
<212> TYPE: DNA
<213> ORGANISM: Aspergillus niger

<400> SEQUENCE: 9
ggaggccatg aagtggacca acgg 24

<210> SEQ ID NO 10
<211> LENGTH: 45
<212> TYPE: DNA
<213> ORGANISM: Aspergillus niger

<400> SEQUENCE: 10
caccgtgaaa gccatgctct ttccttcgtg tagaagacca gacag 45

<210> SEQ ID NO 11
<211> LENGTH: 45
<212> TYPE: DNA
<213> ORGANISM: Aspergillus niger

<400> SEQUENCE: 11
ctggtcttct acacgaagga aagagcatgg ctttcacggt gtctg 45

<210> SEQ ID NO 12
<211> LENGTH: 44
<212> TYPE: DNA
<213> ORGANISM: Aspergillus niger

<400> SEQUENCE: 12
ctatatacac aactggattt accatgggcc cgcggccgca gatc 44

<210> SEQ ID NO 13
<211> LENGTH: 44
<212> TYPE: DNA
<213> ORGANISM: Aspergillus niger

<400> SEQUENCE: 13
gatctgcggc cgcgggccca tggtaaatcc agttgtgtat atag 44

-continued

<210> SEQ ID NO 14
<211> LENGTH: 26
<212> TYPE: DNA
<213> ORGANISM: Aspergillus niger

<400> SEQUENCE: 14
gtcgacatgg tgttttgatc atttta 26

<210> SEQ ID NO 15
<211> LENGTH: 26
<212> TYPE: DNA
<213> ORGANISM: Aspergillus niger

<400> SEQUENCE: 15
ccatggccag ttgtgtatat agagga 26

<210> SEQ ID NO 16
<211> LENGTH: 33
<212> TYPE: DNA
<213> ORGANISM: Aspergillus fumigatus

<400> SEQUENCE: 16
tacacaactg gccatgcgtt tctcccttgc cgc 33

<210> SEQ ID NO 17
<211> LENGTH: 40
<212> TYPE: DNA
<213> ORGANISM: Aspergillus fumigatus

<400> SEQUENCE: 17
agtcacctct agttaattaa ctagcataca gtgcagggct 40

<210> SEQ ID NO 18
<211> LENGTH: 29
<212> TYPE: DNA
<213> ORGANISM: Aspergillus fumigatus

<400> SEQUENCE: 18
cctccaggaa ctggaccgcc acagaactc 29

<210> SEQ ID NO 19
<211> LENGTH: 29
<212> TYPE: DNA
<213> ORGANISM: Aspergillus fumigatus

<400> SEQUENCE: 19
gagttctgtg gcggtccagt tcctggagg 29

<210> SEQ ID NO 20
<211> LENGTH: 36
<212> TYPE: DNA
<213> ORGANISM: Aspergillus fumigatus

<400> SEQUENCE: 20
gctattaatg gggacgggac cttttcctcc agtgtg 36

<210> SEQ ID NO 21
<211> LENGTH: 36
<212> TYPE: DNA
<213> ORGANISM: Aspergillus fumigatus

<400> SEQUENCE: 21
cacactggag gaaaaggtcc cgtccccatt aatagc 36

-continued

```
<210> SEQ ID NO 22
<211> LENGTH: 37
<212> TYPE: DNA
<213> ORGANISM: Aspergillus fumigatus

<400> SEQUENCE: 22

acacaactgg ccatggtcgt cctcagcaag ctcgtca                    37


<210> SEQ ID NO 23
<211> LENGTH: 40
<212> TYPE: DNA
<213> ORGANISM: Aspergillus fumigatus

<400> SEQUENCE: 23

agtcacctct agttaattaa tcagagagca gcaatgatgg                 40


<210> SEQ ID NO 24
<211> LENGTH: 22
<212> TYPE: DNA
<213> ORGANISM: Aspergillus fumigatus

<400> SEQUENCE: 24

ccatggtcca tctatcttca tt                                    22


<210> SEQ ID NO 25
<211> LENGTH: 28
<212> TYPE: DNA
<213> ORGANISM: Aspergillus fumigatus

<400> SEQUENCE: 25

ttaattaatt acaggcactg tgagtacc                              28
```

POLYPEPTIDES HAVING XYLANASE ACTIVITY AND POLYNUCLEOTIDES THEREOF

CROSS-REFERENCE TO RELATED APPLICATIONS

This application is a divisional application of U.S. application Ser. No. 13/151,128, filed Jun. 1, 2011, now U.S. Pat. No. 8,999,694, which is a divisional application of U.S. application Ser. No. 11/054,191, filed Feb. 9, 2005, now U.S. Pat. No. 7,960,160 which claims the benefit of U.S. Provisional Application No. 60,544,461, filed Feb. 12, 2004, U.S. Provisional Application No. 60/544,429, filed Feb. 12, 2004, and U.S. Provisional Application No. 60/544,431, filed Feb. 12, 2004, which applications are incorporated herein by reference.

BACKGROUND OF THE INVENTION

1. Field of the Invention

The present invention relates to isolated polypeptides having xylanase activity and isolated polynucleotides encoding the polypeptides. The invention also relates to nucleic acid constructs, vectors, and host cells comprising the polynucleotides as well as methods for producing and using the polypeptides.

2. Description of the Related Art

Xylan, a major component of plant hemicellulose, is a polymer of D-xylose linked by beta-1,4-xylosidic bonds. Xylan can be degraded to xylose and xylo-oligomers by acid or enzymatic hydrolysis. Enzymatic hydrolysis of xylan produces free sugars without the by-products formed with acid (e.g., furans).

Enzymes capable of degrading xylan and other plant cell wall polysaccharides are important for the food industry, primarily for baking and in fruit and vegetable processing such as fruit juice production or wine making, where their ability to catalyse the degradation of the backbone or side chains of the plant cell wall polysaccharide is utilized (Visser et al., *Xylans and Xylanases*, Proceedings of an International Symposium, Wageningen, The Netherlands, Elsevier Science Publishers, 1992).

Other applications for xylanases are enzymatic breakdown of agricultural wastes for production of alcohol fuels, enzymatic treatment of animal feeds for hydrolysis of pentosans, manufacturing of dissolving pulps yielding cellulose, and bio-bleaching of wood pulp [Detroym R. W. In: Organic Chemicals from Biomass, (CRC Press, Boca Raton, Fla., 1981) 19-41; Paice and Jurasek, *J. Wood Chem. Technol.* 4: 187-198; Pommier and Fuentes, 1989, *Tappi Journal* 187-191; Senior et al., 1988, *Biotechnol. Letters* 10: 907-9121].

WO 92/17573 discloses a substantially pure xylanase derived from *Humicola insolens* and recombinant DNA encoding said xylanase for as a baking agent, a feed additive, and in the preparation of paper and pulp.

WO 92/01793 discloses a xylanase derived from *Aspergillus tubigensis*. It is mentioned, but not shown that related xylanases may be derived from other filamentous fungi, examples of which are *Aspergillus, Disporotrichum, Penicillium, Neurospora, Fusarium* and *Trichoderma*. The xylanases are stated to be useful in the preparation of bread or animal feed, in brewing and in reducing viscosity or improving filterability of cereal starch.

Shei et al., 1985, *Biotech. and Bioeng*. Vol. XXVII, pp. 533-538, and Fournier et al., 1985, *Biotech. and Bioeng*. Vol. XXVII, pp. 539-546, describe purification and characterization of endoxylanases isolated from *Aspergillus niger*.

WO 91/19782 and EP 463 706 discloses xylanase derived from *Aspergillus niger* origin and the recombinant production thereof for use in baking, brewing, paper-making, and treatment of agricultural waste.

WO 03/012071 discloses nucleotide sequences of *Aspergillus fumigatus* xylanases.

It is an object of the present invention to provide new polypeptides having xylanase activity and nucleic acids encoding the polypeptides.

SUMMARY OF THE INVENTION

The present invention relates to isolated polypeptides having xylanase activity selected from the group consisting of:

(a) a polypeptide having an amino acid sequence which has at least 65% identity with amino acids 18 to 364 of SEQ ID NO: 2, at least 85% identity with amino acids 20 to 323 of SEQ ID NO: 4, or at least 80% identity with amino acids 20 to 397 of SEQ ID NO: 6;

(b) a polypeptide which is encoded by a nucleotide sequence which hybridizes under at least low stringency conditions with (i) nucleotides 52 to 1145 of SEQ ID NO: 1, (ii) the cDNA sequence contained in nucleotides 52 to 1145 of SEQ ID NO: 1, or (iii) a complementary strand of (i) or (ii); or under at least medium-high stringency conditions with (iv) nucleotides 58 to 1400 of SEQ ID NO: 3 or nucleotides 107 to 1415 of SEQ ID NO: 5, (v) the cDNA sequence contained in nucleotides 58 to 1400 of SEQ ID NO: 3 or nucleotides 107 to 1415 of SEQ ID NO: 5, or (vi) a complementary strand of (iv) or (v); and (c) a variant comprising a conservative substitution, deletion, and/or insertion of one or more amino acids of amino acids 18 to 364 of SEQ ID NO: 2, amino acids 20 to 323 of SEQ ID NO: 4, or amino acids 20 to 397 of SEQ ID NO: 6.

The present invention also relates to isolated polynucleotides encoding polypeptides having xylanase activity, selected from the group consisting of:

(a) a polynucleotide encoding a polypeptide having an amino acid sequence which has at least 65% identity with amino acids 18 to 364 of SEQ ID NO: 2, at least 85% identity with amino acids 20 to 323 of SEQ ID NO: 4, or at least 80% identity with amino acids 20 to 397 of SEQ ID NO: 6;

(b) a polynucleotide having at least 65% identity with nucleotides 52 to 1145 of SEQ ID NO: 1, at least 85% identity with nucleotides 58 to 1400 of SEQ ID NO: 3, or at least 80% identity with nucleotides 107 to 1415 of SEQ ID NO: 5; and (c) a polynucleotide which hybridizes under at least low stringency conditions with (i) nucleotides 52 to 1145 of SEQ ID NO: 1, (ii) the cDNA sequence contained in nucleotides 52 to 1145 of SEQ ID NO: 1, or (iii) a complementary strand of (i) or (ii); or under at least medium-high stringency conditions with (iv) nucleotides 58 to 1400 of SEQ ID NO: 3 or nucleotides 107 to 1415 of SEQ ID NO: 5, (v) the cDNA sequence contained in nucleotides 58 to 1400 of SEQ ID NO: 3 or nucleotides 107 to 1415 of SEQ ID NO: 5, or (vi) a complementary strand of (iv) or (v).

The present invention also relates to nucleic acid constructs, recombinant expression vectors, and recombinant host cells comprising the polynucleotides.

The present invention also relates to methods for producing such a polypeptide having xylanase activity comprising: (a) cultivating a recombinant host cell comprising a nucleic acid construct comprising a polynucleotide encoding the polypeptide under conditions conducive for production of the polypeptide; and (b) recovering the polypeptide.

The present invention also relates to methods of using the polypeptides in treating pulp, in processes for producing xylose or xylo-oligosaccharide, as feed enhancing enzymes that improve feed digestibility, in baking, and in brewing.

The present invention further relates to nucleic acid constructs comprising a gene encoding a protein, wherein the gene is operably linked to a nucleotide sequence encoding a signal peptide consisting of nucleotides 1 to 51 of SEQ ID NO: 1, nucleotides 1 to 57 of SEQ ID NO: 3, or nucleotides 1 to 106 of SEQ ID NO: 5 or the cDNA thereof, wherein the gene is foreign to the nucleotide sequence.

BRIEF DESCRIPTION OF THE FIGURES

FIGS. 1A and 1B show the genomic DNA sequence and the deduced amino acid sequence of an *Aspergillus fumigatus* Family GH10A xylanase (SEQ ID NOs: 1 and 2, respectively). The predicted signal peptide is underlined and predicted introns are italicized. FIG. 1B is a continuation of the sequences shown in FIG. 1A.

FIG. 4 shows a restriction map of pBM120a.

FIGS. 7A and 7B show the genomic DNA sequence and the deduced amino acid sequence of an *Aspergillus fumigatus* Family GH1OB xylanase (SEQ ID NOs: 3 and 4, respectively). The predicted signal peptide is underlined and predicted introns are italicized. FIG. 7B is a continuation of the sequences shown in FIG. 7A.

FIGS. 9A and 9B show the genomic DNA sequence and the deduced amino acid sequence of an *Aspergillus fumigatus* Family GH10C xylanase (SEQ ID NOs: 5 and 6, respectively). The predicted signal peptide is underlined and predicted introns are italicized. FIG. 9B is a continuation of the sequences shown in FIG. 9A.

DEFINITIONS

Figure 2:
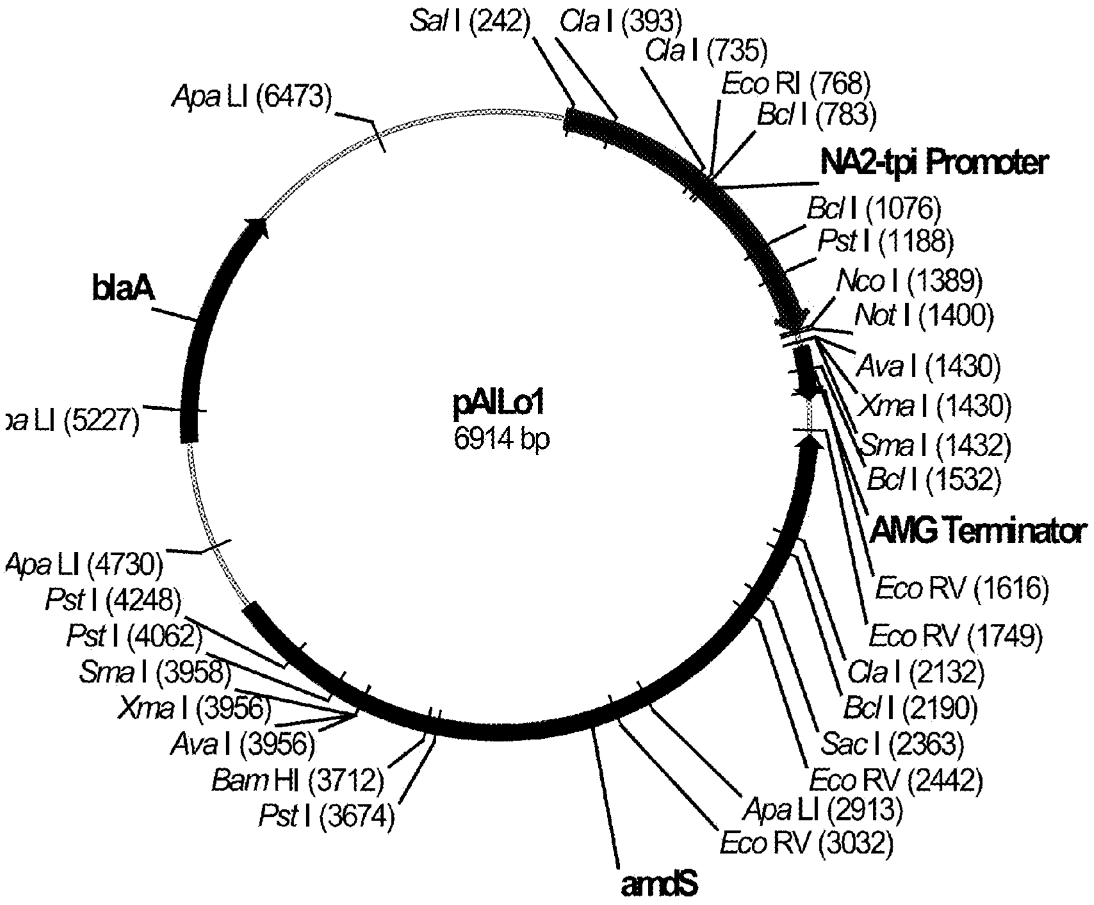
FIG. 2 shows a restriction map of pAILo1.

Xylanase activity: The term "xylanase" is defined herein as a 1,4-beta-D-xylan-xylanohydrolase (E.C. 3.2.1.8) which catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the xylanase activity of the polypeptide consisting of the amino acid sequence shown as amino acids 18 to 364 of SEQ ID NO: 2, amino acids 20 to 323 of SEQ ID NO: 4, or amino acids 20 to 397 of SEQ ID NO: 6.

Family GH10 xylanase: The term "Family 10 glycoside hydrolase" or "Family GH10" is defined herein as a polypeptide falling into the glycoside hydrolase Family 10 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Identity: The relatedness between two amino acid sequences or between two nucleotide sequences is described by the parameter "identity".

For purposes of the present invention, the degree of identity between two amino acid sequences is determined by the Clustal method (Higgins, 1989, *CABIOS* 5: 151-153) using the LASERGENE® MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

For purposes of the present invention, the degree of identity between two nucleotide sequences is determined by the Wilbur-Lipman method (Wilbur and Lipman, 1983, *Proceedings of the National Academy of Science USA* 80: 726-730) using the LASERGENE® MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

Polypeptide fragment: The term "polypeptide fragment" is defined herein as a polypeptide having one or more amino acids deleted from the amino and/or carboxyl terminus of SEQ ID NO: 2, 4, or 6, or a homologous sequence thereof, wherein the fragment has xylanase activity.

Preferably, a fragment of SEQ ID NO: 2 contains at least 300 amino acid residues, more preferably at least 315 amino acid residues, and most preferably at least 330 amino acid residues.

Preferably, a fragment of SEQ ID NO: 4 contains at least 255 amino acid residues, more preferably at least 270 amino acid residues, and most preferably at least 285 amino acid residues.

Preferably, a fragment of SEQ ID NO: 6 contains at least 320 amino acid residues, more preferably at least 340 amino acid residues, and most preferably at least 360 amino acid residues.

Subsequence: The term "subsequence" is defined herein as a nucleotide sequence having one or more nucleotides deleted from the 5' and/or 3' end of SEQ ID NO: 1, 3, or 5, or a homologous sequence thereof, wherein the subsequence encodes a polypeptide fragment having xylanase activity.

Preferably, a subsequence of SEQ ID NO: 1 contains at least 900 nucleotides, more preferably at least 945 nucleotides, and most preferably at least 990 nucleotides.

Preferably, a subsequence of SEQ ID NO: 3 contains at least 765 nucleotides, more preferably at least 810 nucleotides, and most preferably at least 855 nucleotides.

Preferably, a subsequence of SEQ ID NO: 5 contains at least 960 nucleotides, more preferably at least 1020 nucleotides, and most preferably at least 1080 nucleotides.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide which is at least 20% pure, preferably at least 40% pure, more preferably at least 60% pure, even more preferably at least 80% pure, most preferably at least 90% pure, and even most preferably at least 95% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG and TGA. The coding sequence may be a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct or expression vector comprising a polynucleotide of the present invention.

Modification: The term "modification" means herein any chemical modification of the polypeptide consisting of amino acids 18 to 364 of SEQ ID NO: 2, amino acids 20 to 323 of SEQ ID NO: 4, or amino acids 20 to 397 of SEQ ID NO: 6, or a homologous sequence thereof, as well as genetic manipulation of the DNA encoding that polypeptide. The modification can be substitutions, deletions and/or insertions of one or more amino acids as well as replacements of one or more amino acid side chains.

Artificial variant: When used herein, the term "artificial variant" means a polypeptide having xylanase activity produced by an organism expressing a modified nucleotide sequence of SEQ ID NO: 1, 3, or 5, or a homologous sequence thereof, or the mature coding region thereof. The modified nucleotide sequence is obtained through human intervention by modification of the nucleotide sequence disclosed in SEQ ID NO: 1, 3, or 5, or a homologous sequence thereof, or the mature coding region thereof.

DETAILED DESCRIPTION OF THE INVENTION

Polypeptides Having Xylanase Activity

In a first aspect, the present invention relates to isolated polypeptides having an amino acid sequence which has a degree of identity to amino acids 18 to 364 of SEQ ID NO: 2 (i.e., the mature polypeptide) of at least 65%, preferably at least 70%, more preferably at least 75%, more preferably at least 80%, more preferably at least 85%, even more preferably at least 90%, most preferably at least 95%, and even most preferably at least 97%, 98%, or 99%, which have xylanase activity; a degree of identity to amino acids 20 to 323 of SEQ ID NO: 4 (i.e., the mature polypeptide) of at least 85%, preferably at least 90%, more preferably at least 95%, and most preferably at least 97%, 98%, or 99%, which have xylanase activity; or a degree of identity to amino acids 20 to 397 of SEQ ID NO: 6 (i.e., the mature polypeptide) of at least 80%, preferably at least 85%, more preferably at least 90%, more preferably at least 95%, and most preferably at least 97%, 98%, or 99%, which have xylanase activity (hereinafter "homologous polypeptides"). In a preferred aspect, the homologous polypeptides have an amino acid sequence which differs by ten amino acids, preferably by five amino acids, more preferably by four amino acids, even more preferably by three amino acids, most preferably by two amino acids, and even most preferably by one amino acid from amino acids 18 to 364 of SEQ ID NO: 2, amino acids 20 to 323 of SEQ ID NO: 4, or amino acids 20 to 397 of SEQ ID NO: 6.

A polypeptide of the present invention preferably comprises the amino acid sequence of SEQ ID NO: 2 or an allelic variant thereof; or a fragment thereof that has xylanase activity. In a preferred aspect, a polypeptide comprises the amino acid sequence of SEQ ID NO: 2. In another preferred aspect, a polypeptide comprises amino acids 18 to 364 of SEQ ID NO: 2, or an allelic variant thereof; or a fragment thereof that has xylanase activity. In another preferred aspect, a polypeptide comprises amino acids 18 to 364 of SEQ ID NO: 2. In another preferred aspect, a polypeptide consists of the amino acid sequence of SEQ ID NO: 2 or an allelic variant thereof; or a fragment thereof that has xylanase activity. In another preferred aspect, a polypeptide consists of the amino acid sequence of SEQ ID NO: 2. In another preferred aspect, a polypeptide consists of amino acids 18 to 364 of SEQ ID NO: 2 or an allelic variant thereof; or a fragment thereof that has xylanase activity. In another preferred aspect, a polypeptide consists of amino acids 18 to 364 of SEQ ID NO: 2.

A polypeptide of the present invention also preferably comprises the amino acid sequence of SEQ ID NO: 4 or an allelic variant thereof; or a fragment thereof that has xylanase activity. In a preferred aspect, a polypeptide comprises the amino acid sequence of SEQ ID NO: 4. In another preferred aspect, a polypeptide comprises amino acids 20 to 323 of SEQ ID NO: 4, or an allelic variant thereof; or a fragment thereof that has xylanase activity. In another preferred aspect, a polypeptide comprises amino acids 20 to 323 of SEQ ID NO: 4. In another preferred aspect, a polypeptide consists of the amino acid sequence of SEQ ID NO: 4 or an allelic variant thereof; or a fragment thereof that has xylanase activity. In another preferred aspect, a polypeptide consists of the amino acid sequence of SEQ ID NO: 4. In another preferred aspect, a polypeptide consists of amino acids 20 to 323 of SEQ ID NO: 4 or an allelic variant thereof; or a fragment thereof that has xylanase activity. In another preferred aspect, a polypeptide consists of amino acids 20 to 323 of SEQ ID NO: 4.

A polypeptide of the present invention also preferably comprises the amino acid sequence of SEQ ID NO: 6 or an allelic variant thereof; or a fragment thereof that has xylanase activity. In a preferred aspect, a polypeptide comprises the amino acid sequence of SEQ ID NO: 6. In another preferred aspect, a polypeptide comprises amino acids 20 to 397 of SEQ ID NO: 6, or an allelic variant thereof; or a fragment thereof that has xylanase activity. In another preferred aspect, a polypeptide comprises amino acids 20 to 397 of SEQ ID NO: 6. In another preferred aspect, a polypeptide consists of the amino acid sequence of SEQ ID NO: 6 or an allelic variant thereof; or a fragment thereof that has xylanase activity. In another preferred aspect, a polypeptide consists of the amino acid sequence of SEQ ID NO: 6. In another preferred aspect, a polypeptide consists of amino acids 20 to 397 of SEQ ID NO: 6 or an allelic variant thereof; or a fragment thereof that has xylanase activity. In another preferred aspect, a polypeptide consists of amino acids 20 to 397 of SEQ ID NO: 6.

In a second aspect, the present invention relates to isolated polypeptides having xylanase activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 52 to 1145 of SEQ ID NO: 1, nucleotides 58 to 1400 of SEQ ID NO: 3, or nucleotides 107 to 1415 of SEQ ID NO: 5, (ii) the cDNA sequence contained in nucleotides 52 to 1145 of SEQ ID NO: 1, nucleotides 58 to 1400 of SEQ ID NO: 3, or nucleotides 107 to 1415 of SEQ ID NO: 5, (iii) a subsequence of (i) or (ii), or (iv) a complementary strand of (i), (ii), or (iii) (J. Sambrook, E. F. Fritsch, and T. Maniatis, 1989, *Molecular Cloning, A Laboratory Manual,* 2d edition, Cold Spring Harbor, N.Y.). A subsequence of SEQ ID NO: 1, 3, or 5 contains at least 100 contiguous nucleotides or preferably at least 200 contiguous nucleotides. Moreover, the subsequence may encode a polypeptide fragment which has xylanase activity.

The nucleotide sequence of SEQ ID NO: 1, 3, or 5, or a subsequence thereof, as well as the amino acid sequence of SEQ ID NO: 2, 4, or 6, or a fragment thereof, may be used to design a nucleic acid probe to identify and clone DNA encoding polypeptides having xylanase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other organisms may, therefore, be screened for DNA which hybridizes with the probes described above and which encodes a polypeptide having xylanase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1, 3, or 5, or a subsequence thereof, the carrier material is used in a Southern blot.

For purposes of the present invention, hybridization indicates that the nucleotide sequence hybridizes to a labeled nucleic acid probe corresponding to the nucleotide sequence shown in SEQ ID NO: 1, 3, or 5, the cDNA sequence contained in SEQ ID NO: 1, 3, or 5, its complementary strand, or a subsequence thereof, under very low to very high stringency conditions. Molecules to which the nucleic acid probe hybridizes under these conditions can be detected using X-ray film.

In a preferred embodiment, the nucleic acid probe is a nucleic acid sequence which encodes the polypeptide of SEQ ID NO: 2, or a subsequence thereof. In another preferred embodiment, the nucleic acid probe is SEQ ID NO: 1. In another preferred embodiment, the nucleic acid probe is the mature polypeptide coding region of SEQ ID NO: 1. In another preferred embodiment, the nucleic acid probe is the nucleic acid sequence contained in plasmid pSMO210 which is contained in *Escherichia coli* NRRL B-30706, wherein the nucleic acid sequence encodes a polypeptide having xylanase activity. In another preferred embodiment, the nucleic acid probe is the mature polypeptide coding region contained in plasmid pSMO210 which is contained in *Escherichia coli* NRRL B-30706.

In another preferred embodiment, the nucleic acid probe is a nucleic acid sequence which encodes the polypeptide of SEQ ID NO: 4, or a subsequence thereof. In another preferred embodiment, the nucleic acid probe is SEQ ID NO: 3. In another preferred embodiment, the nucleic acid probe is the mature polypeptide coding region of SEQ ID NO: 3.

In another preferred embodiment, the nucleic acid probe is the nucleic acid sequence contained in plasmid pJLin162 which is contained in *Escherichia coli* NRRL B-30702, wherein the nucleic acid sequence encodes a polypeptide having xylanase activity. In another preferred embodiment, the nucleic acid probe is the mature polypeptide coding region contained in plasmid pJLin162 which is contained in *Escherichia coli* NRRL B-30702.

In a preferred embodiment, the nucleic acid probe is a nucleic acid sequence which encodes the polypeptide of SEQ ID NO: 6, or a subsequence thereof. In another preferred embodiment, the nucleic acid probe is SEQ ID NO: 5. In another preferred embodiment, the nucleic acid probe is the mature polypeptide coding region of SEQ ID NO: 5. In another preferred embodiment, the nucleic acid probe is the nucleic acid sequence contained in plasmid pHyGe009 which is contained in *Escherichia coli* NRRL B-30703, wherein the nucleic acid sequence encodes a polypeptide having xylanase activity. In another preferred embodiment, the nucleic acid probe is the mature polypeptide coding region contained in plasmid pHyGe009 which is contained in *Escherichia coli* NRRL B-30703.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to artificial variants comprising a conservative substitution, deletion, and/or insertion of one or more amino acids of SEQ ID NO: 2, 4, or 6, or a homologous sequence thereof; or the mature polypeptide thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., xylanase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of amino acids 18 to 364 of SEQ ID NO: 2, amino acids 20 to 323 of SEQ ID NO: 4, or amino acids 20 to 397 of SEQ ID NO: 6 is 10, preferably 9, more preferably 8, more preferably 7, more preferably at most 6, more preferably 5, more preferably 4, even more preferably 3, most preferably 2, and even most preferably 1.

Sources of Polypeptides Having Xylanase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a bacterial polypeptide. For example, the polypeptide may be a gram positive bacterial polypeptide such as a *Bacillus* polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis polypeptide;* or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

A polypeptide of the present invention may also be a fungal polypeptide, and more preferably a yeast polypeptide such as a *Candida, Kluyveromyces, Pichia, Saccharomyces, Schizosaccharomyces*, or *Yarrowia* polypeptide; or more preferably a filamentous fungal polypeptide such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma* polypeptide.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having xylanase activity.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium*

*roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei*, or *Trichoderma viride* polypeptide.

In a more preferred embodiment, the polypeptide is an *Aspergillus fumigatus* polypeptide, e.g., the polypeptide with the amino acid sequence of SEQ ID NO: 2, 4, or 6.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides having a nucleotide sequence which encode a polypeptide of the present invention.

In a preferred aspect, the nucleic acid sequence is set forth in SEQ ID NO: 1. In another more preferred embodiment, the nucleic acid sequence is the sequence contained in plasmid pSMO210 that is contained in *Escherichia coli* NRRL B-30706. In another preferred aspect, the nucleic acid sequence is the mature polypeptide coding region of SEQ ID NO: 1. In another more preferred aspect, the nucleic acid sequence is the mature polypeptide coding region contained in plasmid pSMO210 that is contained in *Escherichia coli* NRRL B-30706. The present invention also encompasses nucleic acid sequences which encode a polypeptide having the amino acid sequence of SEQ ID NO: 2 or the mature polypeptide thereof, which differ from SEQ ID NO: 1 by virtue of the degeneracy of the genetic code. The present invention also relates to subsequences of SEQ ID NO: 1 which encode fragments of SEQ ID NO: 2 that have xylanase activity.

In another preferred embodiment, the nucleic acid sequence is set forth in SEQ ID NO: 3. In another more preferred embodiment, the nucleic acid sequence is the sequence contained in plasmid pJLin162 that is contained in *Escherichia coli* NRRL B-30702. In another preferred embodiment, the nucleic acid sequence is the mature polypeptide coding region of SEQ ID NO: 3. In another more preferred embodiment, the nucleic acid sequence is the mature polypeptide coding region contained in plasmid pJLin162 that is contained in *Escherichia coli* NRRL B-30702. The present invention also encompasses nucleic acid sequences which encode a polypeptide having the amino acid sequence of SEQ ID NO: 4 or the mature polypeptide thereof, which differ from SEQ ID NO: 3 by virtue of the degeneracy of the genetic code. The present invention also relates to subsequences of SEQ ID NO: 3 which encode fragments of SEQ ID NO: 4 that have xylanase activity.

In a preferred embodiment, the nucleic acid sequence is set forth in SEQ ID NO: 5. In another more preferred embodiment, the nucleic acid sequence is the sequence contained in plasmid pHyGe009 that is contained in *Escherichia coli* NRRL B-30703. In another preferred embodiment, the nucleic acid sequence is the mature polypeptide coding region of SEQ ID NO: 5. In another more preferred embodiment, the nucleic acid sequence is the mature polypeptide coding region contained in plasmid pHyGe009 that is contained in *Escherichia coli* NRRL B-30703. The present invention also encompasses nucleic acid sequences which encode a polypeptide having the amino acid sequence of SEQ ID NO: 6 or the mature polypeptide thereof, which differ from SEQ ID NO: 5 by virtue of the degeneracy of the genetic code. The present invention also relates to subsequences of SEQ ID NO: 5 which encode fragments of SEQ ID NO: 6 that have xylanase activity.

The present invention also relates to mutant polunucleotides comprising at least one mutation in the mature polypeptide coding sequence of SEQ ID NO: 1, 3, or 5, in which the mutant nucleotide sequence encodes a polypeptide which consists of amino acids 18 to 364 of SEQ ID NO: 2, amino acids 20 to 323 of SEQ ID NO: 4, or amino acids 20 to 397 of SEQ ID NO: 6, respectively.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application,* Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Aspergillus*, or another or related organism and thus, for example, may be an allelic or species variant of the polypeptide encoding region of the nucleotide sequence.

The present invention also relates to polynucleotides having nucleotide sequences which have a degree of identity to the mature polypeptide coding sequence of SEQ ID NO: 1 (i.e., nucleotides 52 to 1145 of SEQ ID NO: 1) of at least 65%, preferably at least 70%, more preferably at least 75%, more preferably at least 80%, more preferably at least 85%, more preferably at least 90%, even more preferably at least 95%, and most preferably at least 97%, 98%, or 99% identity, which encode an active polypeptide.

The present invention also relates to polynucleotides having nucleotide sequences which have a degree of identity to the mature polypeptide coding sequence of SEQ ID NO: 3 (i.e., nucleotides 58 to 1400) of at least 85%, preferably at least 90%, more preferably at least 95%, and most preferably at least 97%, 98%, or 99% identity, which encode an active polypeptide.

The present invention also relates to polynucleotides having nucleotide sequences which have a degree of identity to the mature polypeptide coding sequence of SEQ ID NO: 5 (i.e., nucleotides 107 to 1415) of at least 80%, preferably at least 85%, more preferably at least 90%, even more preferably at least 95%, and most preferably at least 97%, 98%, or 99% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO: 1, 3, or 5, e.g., a subsequence thereof, and/or by introduction of nucleotide substitutions which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989*, Science* 244: 1081-1085). In the latter technique, mutations are introduced at every positively charged residue in the molecule, and the resultant mutant molecules are tested for xylanase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The present invention also relates to isolated polynucleotides encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) nucleotides 52 to 1145 of SEQ ID NO: 1, nucleotides 58 to 1400 of SEQ ID NO: 3, or nucleotides 107 to 1415 of SEQ ID NO: 5, (ii) the cDNA sequence contained in nucleotides 52 to 1145 of SEQ ID NO: 1, nucleotides 58 to 1400 of SEQ ID NO: 3, or nucleotides 107 to 1415 of SEQ ID NO: 5, or (iii) a complementary strand of (i) or (ii); or allelic variants and subsequences thereof (Sambrook et al., 1989, supra), as defined herein.

The present invention also relates to isolated polynucleotides obtained by (a) hybridizing a population of DNA under very low, low, medium, medium-high, high, or very high stringency conditions with (i) nucleotides 52 to 1145 of SEQ ID NO: 1, nucleotides 58 to 1400 of SEQ ID NO: 3, or nucleotides 107 to 1415 of SEQ ID NO: 5, (ii) the cDNA sequence contained in nucleotides 52 to 1145 of SEQ ID NO: 1, nucleotides 58 to 1400 of SEQ ID NO: 3, or nucleotides 107 to 1415 of SEQ ID NO: 5, or (iii) a complementary strand of (i) or (ii); and (b) isolating the hybridizing polynucleotides, which encode a polypeptide having xylanase activity.

Nucleic Acid Constructs

The present invention also relates to nucleic acid constructs comprising an isolated polynucleotide of the present invention operably linked to one or more control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences* USA 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase,

*Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice, i.e., secreted into a culture medium, may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

In a preferred aspect, the signal peptide coding region is nucleotides 1 to 51 of SEQ ID NO: 1 which encode amino acids 1 to 17 of SEQ ID NO: 2.

In a preferred aspect, the signal peptide coding region is nucleotides 1 to 57 of SEQ ID NO: 3 which encode amino acids 1 to 19 of SEQ ID NO: 4.

In a preferred aspect, the signal peptide coding region is nucleotides 1 to 106 of SEQ ID NO: 5, or the cDNA thereof, which encode amino acids 1 to 19 of SEQ ID NO: 6.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli,* and pUB110, pE194, pTA1060, and pAMR1 permitting replication in *Bacillus.*

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus cell*, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis;* or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus, Bacillus licheniformis, Bacillus stearothermophilus*, or *Bacillus subtilis* cell. In another preferred aspect, the *Bacillus* cell is an alkalophilic *Bacillus.*

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizen, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series No.* 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola*

*lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming Fusarium species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, comprising: (a) cultivating a cell, which in its wild-type form is capable of producing the polypeptide, under conditions conducive for production of the polypeptide; and (b) recovering the polypeptide. Preferably, the cell is of the genus *Aspergillus* and more preferably *Aspergillus fumigatus*.

The present invention also relates to methods for producing a polypeptide of the present invention, comprising: (a) cultivating a host cell under conditions conducive for production of the polypeptide; and (b) recovering the polypeptide.

The present invention also relates to methods for producing a polypeptide of the present invention, comprising: (a) cultivating a host cell under conditions conducive for production of the polypeptide, wherein the host cell comprises a mutant nucleotide sequence having at least one mutation in the mature polypeptide coding region of SEQ ID NO: 1, wherein the mutant nucleotide sequence encodes a polypeptide which consists of amino acids 18 to 364 of SEQ ID NO: 2, amino acids 20 to 323 of SEQ ID NO: 4, or amino acids 20 to 397 of SEQ ID NO: 6, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Plants

The present invention also relates to a transgenic plant, plant part, or plant cell which has been transformed with a nucleotide sequence encoding a polypeptide having xylanase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more expression constructs encoding a polypeptide of the present invention into the plant host genome or chloroplast genome and propagating the resulting modified plant or plant cell into a transgenic plant or plant cell.

The expression construct is conveniently a nucleic acid construct which comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a Vicia faba promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods for producing a polypeptide of the present invention comprising: (a) cultivating a transgenic plant or a plant cell comprising a polynucleotide encoding a polypeptide having xylanase activity of the present invention under conditions conducive for production of the polypeptide; and (b) recovering the polypeptide.

Removal or Reduction of Xylanase Activity

The present invention also relates to methods for producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence which is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred embodiment, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell which comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising: (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of xylanase activity by fermentation of a cell which produces both a polypeptide of the present invention as well as the protein product of interest by adding an effective amount of an agent capable of inhibiting xylanase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of xylanase activity by cultivating the cell under conditions permitting the expression of the product, subjecting the resultant culture broth to a combined pH and temperature treatment so as to reduce the xylanase activity substantially, and recovering the product from the culture broth. Alternatively, the combined pH and temperature treatment may be performed on an enzyme preparation recovered from the culture broth. The combined pH and temperature treatment may optionally be used in combination with a treatment with a xylanase inhibitor.

In accordance with this aspect of the invention, it is possible to remove at least 60%, preferably at least 75%, more preferably at least 85%, still more preferably at least 95%, and most preferably at least 99% of the xylanase activity. Complete removal of xylanase activity may be obtained by use of this method.

The combined pH and temperature treatment is preferably carried out at a pH of 4-5 and a temperature of 80-90° C. for a sufficient period of time to attain the desired effect, where typically, 30 to 60 minutes is sufficient.

The methods used for cultivation and purification of the product of interest may be performed by methods known in the art.

The methods of the present invention for producing an essentially xylanase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellobiohydrolase, cellulase, chitinase, cutinase, cyclodextrin glycosyltransferase, deoxyribonuclease, endoglucanase, esterase, galactosidase, beta-galactosidase, glucoamylase, glucose oxidase, alpha- or beta-glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or another xylanase. The xylanase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from xylanase activity which is produced by a method of the present invention.

Compositions

The present invention also relates to compositions comprising a polypeptide of the present invention. Preferably, the compositions are enriched in such a polypeptide. The term "enriched" indicates that the xylanase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or nother xylanase. The additional enzyme(s) may be produced, for example, by a microorganism belonging to the genus *Aspergillus*, preferably *Aspergillus aculeatus, Aspergillus awamori, Aspergillus fumigatus, Aspergillus foetidus, Aspergillus japonicus, Aspergillus nidulans, Aspergillus niger*, or *Aspergillus oryzae; Fusarium,* preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides*, or *Fusarium venenatum; Humicola*, preferably *Humicola insolens* or *Humicola lanuginosa;* or *Trichoderma*, preferably *Trichoderma harzianum, Trichoderma koningii, Trichoderma longibrachiatum, Trichoderma reesei*, or *Trichoderma viride.*

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

A polypeptide having xylanase activity of the present invention may be used in several applications to degrade or convert a xylan-containing material by treating the material with an effective amount of the polypeptide (see, for example, WO 2002/18561).

The polypeptides may be used in methods for the treatment of pulp according to U.S. Pat. No. 5,658,765.

The polypeptides may also be used in processes for producing xylose or xylo-oligosaccharide according to U.S. Pat. No. 5,658,765.

The polypeptides may also be used as feed enhancing enzymes that improve feed digestibility to increase the efficiency of its utilization according to U.S. Pat. No. 6,245,546.

The polypeptides may also be used in baking according to U.S. Pat. No. 5,693,518.

The polypeptides may further be used in brewing according to WO 2002/24926.

Signal Peptide

The present invention also relates to nucleic acid constructs comprising a gene encoding a protein operably linked to a nucleotide sequence consisting of a signal peptide consisting of nucleotides 1 to 51 of SEQ ID NO: 1, nucleotides 1 to 57 of SEQ ID NO: 3, or nucleotides 1 to 106 of SEQ ID NO: 5, or the cDNA thereof, encoding a signal peptide consisting of amino acids 1 to 17 of SEQ ID NO: 2, amino acids 1 to 19 of SEQ ID NO: 4, or amino acids 1 to 19 of SEQ ID NO: 6, respectively, which allows secretion of the protein into a culture medium, wherein the gene is foreign to the nucleotide sequence.

The present invention also relates to recombinant expression vectors and recombinant host cells comprising such nucleic acid constructs.

The present invention also relates to methods for producing a protein comprising: (a) cultivating such a recombinant host cell under conditions suitable for production of the protein; and (b) recovering the protein.

The first and second nucleotide sequences may be operably linked to foreign genes individually with other control sequences or in combination with other control sequences. Such other control sequences are described supra. As described earlier, where both signal peptide and propeptide regions are present at the amino terminus of a protein, the propeptide region is positioned next to the amino terminus of a protein and the signal peptide region is positioned next to the amino terminus of the propeptide region.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Materials

Chemicals used as buffers and substrates were commercial products of at least reagent grade.

Strains

*Aspergillus oryzae* BECh2 strain (Δalp, Δamy, CPA-, KA-, Δnp1) was used for expression of the *Aspergillus fumigatus* xylanase. *Aspergillus fumigatus* PaHa34 was used as the source of the Family 10 xylanase.

Media

Minimal medium was composed per liter of 6 g of $NaNO_3$, 0.52 g of KCl, 1.52 g of $KH_2PO_4$, 1 ml of COVE trace elements solution, 20 g of Noble agar, 1% glucose, and 0.5% $MgSO_4.7H_2O$.

COVE plates were composed per liter of 342.3 g of sucrose, 20 ml of COVE salt solution, 10 ml of 1 M acetamide, 10 ml of 1.5 M $CsCl_2$, and 25 g of Noble agar.

COVE salt solution was composed per liter of 26 g of KCl, 26 g of $MgSO_4.7H_2O$, 76 g of $KH_2PO_4$, and 50 ml of COVE trace metals solution.

COVE trace elements solution was composed per liter of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, and 10 g of $ZnSO_4.7H_2O$.

MY25 medium was composed per liter of 25 g of maltodextrin, 2 g of $MgSO_4.7H_2O$, 10 g of $KH_2PO_4$, 2 g of citric acid, 2 g of $K_2SO_4$, 2 g of urea, 10 g of yeast extract, and 1.5 ml of AMG trace metals solution, adjusted to pH 6.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, and 3 g of citric acid.

LB medium was composed per liter of 10 g of tryptone, 5 g of yeast extract, and 5 g of NaCl.

2X YT medium was composed per liter of 16 g of tryptone, 10 g of yeast extract, and 5 g of NaCl. 2X YT plates were composed per liter of 16 g of tryptone, 10 g of yeast extract, 5 g of NaCl and 15 g of Noble agar.

SOC medium was composed per liter of 20 g of tryptone, 5 g of yeast extract, 2 ml of 5 M NaCl, and 2.5 ml of 1 M KCl.

Example 1

Identification of a Family GH10 Xylanase Gene in the Genomic Sequence of *Aspergillus Fumigatus*

A tfasty search (Pearson, W. R., 1999, in *Bioinformatics Methods and Protocols*, S. Misener and S. A. Krawetz, ed., pp. 185-219) of the *Aspergillus fumigatus* partial genome sequence (The Institute for Genomic Research, Rockville, Md.) was carried out using as query a Family 10 xylanase protein sequence from *Aspergillus kawachii* (Accession No. P33559). Several genes were identified as putative Family GH10 homologs based upon a high degree of similarity to the query sequence at the amino acid level. Three genomic regions of approximately 3000 by with greater than 70% identity to the query sequence at the amino acid level were identified.

Example 2

*Aspergillus Fumigatus* Genomic DNA Extraction

*Aspergillus fumigatus* was grown in 250 ml of potato dextrose medium in a baffled shake flask at 37° C. and 240 rpm. Mycelia were harvested by filtration, washed twice in TE (10 mM Tris-1 mM EDTA), and frozen under liquid nitrogen. Frozen mycelia were ground, by mortar and pestle, to a fine powder, which was resuspended in pH 8.0 buffer containing 10 mM Tris, 100 mM EDTA, 1% TRITON® X-100, 0.5 M guanidine-HCl, and 200 mM NaCl. DNase-free RNase A was added at a concentration of 20 mg per liter and the lysate was incubated at 37° C. for 30 minutes. Cellular debris was removed by centrifugation, and DNA was isolated by using QIAGEN® Maxi 500 columns (QIAGEN Inc., Valencia, Calif.). The columns were equilibrated in 10 ml of QBT washed with 30 ml of QC, and eluted with 15 ml of QF (all buffers from QIAGEN Inc., Valencia, Calif.). DNA was precipitated in isopropanol, washed in 70% ethanol, and recovered by centrifugation. The DNA was resuspended in TE buffer.

Example 3

Construction of pAlLo1 Expression Vector

Expression vector pAlLo1 was constructed by modifying pBANe6 (U.S. Pat. No. 6,461,837), which comprises a hybrid of the promoters from the genes for *Aspergillus niger* neutral alpha-amylase and *Aspergillus oryzae* triose phosphate isomerase (NA2-tpi promoter), *Aspergillus niger* amyloglucosidase terminator sequence (AMG terminator), and *Aspergillus nidulans* acetamidase gene (amdS). All mutagenesis steps were verified by sequencing using BIGDYE™ terminator chemistry (Applied Biosystems, Inc., Foster City, Calif.). Modification of pBANe6 was performed by first eliminating three NcoI restriction sites at positions 2051, 2722, and 3397 by from the amdS selection marker by site-directed mutagenesis. All changes were designed to be "silent" leaving the actual protein sequence of the amdS gene product unchanged. Removal of these three sites was performed simultaneously with a GENEEDITOR™ in vitro Site-Directed Mutagenesis Kit (Promega, Madison, Wis.) according to the manufacturer's instructions using the following primers (underlined nucleotide represents the changed base):

AMDS3NcoMut (2050):
(SEQ ID NO: 7)
5'-GTGCCCCATGATACGCCTCCGG-3'

AMDS2NcoMut (2721):
(SEQ ID NO: 8)
5'-GAGTCGTATTTCCAAGGCTCCTGACC-3'

AMDS1NcoMut (3396):
(SEQ ID NO: 9)
5'-GGAGGCCATGAAGTGGACCAACGG-3'

A plasmid comprising all three expected sequence changes was then submitted to site-directed mutagenesis, using a QUICKCHANGE™ Site-Directed Mutagenesis Kit (Stratagene, La Jolla, Calif.), to eliminate the Nco I restriction site at the end of the AMG terminator at position 1643. The following primers (underlined nucleotide represents the changed base) were used for mutagenesis:

Upper Primer to mutagenize the AMG terminator sequence:
(SEQ ID NO: 10)
5'-CACCGTGAAAGCCATGCTCTTTCCTTCGTGTAGAA
GACCAGACAG-3'

-continued

```
Lower Primer to mutagenize the AMG
terminator sequence:
                                    (SEQ ID NO: 11)
5'-CTGGTCTTCTACACGAAGGAAAGAGCATGGCTTTC
ACGGTGTCTG-3'
```

The last step in the modification of pBANe6 was the addition of a new NcoI restriction site at the beginning of the polylinker using a QUICKCHANGE™ Site-Directed Mutagenesis Kit and the following primers (underlined nucleotides represent the changed bases) to yield pAlLo1 (FIG. 2).

```
Upper Primer to mutagenize the NA2-tpi promoter:
                                    (SEQ ID NO: 12)
5'-CTATATACACAACTGGATTTACCATGGGCCCGCG
GCCGCAGATC-3'

Lower Primer to mutagenize the NA2-tpi promoter:
                                    (SEQ ID NO: 13)
5'-GATCTGCGGCCGCGGGCCCATGGTAAATCCAGTT
GTGTATATAG-3'
```

Example 4

Construction of pBM120a Expression Vector

Plasmid pBM120a was constructed to obtain a plasmid containing a double NA2 promoter (NA2-NA2-tpi) for driving gene expression in *Aspergillus* species, and containing the ampicillin resistance gene for selection in *E. coli.*

Primers were designed to PCR amplify the double NA2 promoter from pJaL721 (WO 03/008575). Restriction enzyme sites Sal I and Nco I (underlined) were added for cloning the double promoter into the *Aspergillus* expression plasmid pAlLo1.

```
                                    (SEQ ID NO: 14)
5'-GTCGACATGGTGTTTTGATCATTTTA-3'

                                    (SEQ ID NO: 15)
5'-CCATGGCCAGTTGTGTATATAGAGGA-3'
```

The fragment of interest was amplified by PCR using the EXPAND® High Fidelity PCR System (Roche Diagnostics, Mannheim, Germany). The PCR amplification reaction mixture contained 1 μl of 0.09 μg of pJaL721, 1 μl of each of the primers (50 pmol/μl), 5 μl of 10×PCR buffer with 15 mM $MgCl_2$, 1 μl of a dATP, dTTP, dGTP, and dCTP mix (10 mM each), 37.25 μl of water, and 0.75 μl (3.5 U/μl) of DNA polymerase mix. An EPPENDORF® MASTERCYCLER® thermocycler was used to amplify the fragment with the following settings: 1 cycle at 94° C. for 2 minutes; 10 cycles each at 94° C. for 15 seconds, 55° C. for 30 seconds, 72° C. for 1.25 minutes; 15 cycles each at 94° C. for 15 seconds, 55° C. for 30 seconds, 72° C. for 1.25 minutes plus 5 second elongation at each successive cycle; 1 cycle at 72° C. for 7 minutes; and a 10° C. hold. Ten microliters of this PCR reaction was mixed with 1 μl of 10× DNA loading dye (25% glycerol, 10 mM Tris pH 7.0, 10 mM EDTA, 0.025% bromophenol blue, 0.025% xylene cyanol) and run on a 1.0% (w/v) agarose gel using 40 mM Tris base-20 mM sodium acetate-1 mM disodium EDTA (TAE) buffer. An 1128 by PCR product was observed with UV light on a NUCLEOTECH® gel visualization system (Nucleotech, San Mateo, Calif.). The PCR product was directly ligated into pCR®2.1-TOPO (Invitrogen, Carlsbad, Calif.) according to the manufacturer's instructions. A 1 μl volume of fresh PCR product, 3 μl of double-distilled water, and 1 μl of the TOPO cloning vector were mixed with a pipette and incubated on the bench top for 5 minutes.

After the incubation, 2 μl of the mixture was used to transform ONE SHOT® competent *E. coli* cells (Invitrogen, Carlsbad, Calif.). A 2 μl volume of the ligation mixture was added to the *E. coli* cells and incubated on ice for 5 minutes. Subsequently, the cells were heat shocked for 30 seconds at 42° C., and then placed on ice for 2 minutes. A 250 μl volume of SOC medium was added to these cells and the mixture was incubated for 1 hour at 37° C. and 250 rpm. After the incubation the colonies were spread on 2× YT plates supplemented with 100 μg of ampicillin per ml and incubated at 37° C. overnight for selection of the plasmid. Eight colonies that grew on the plates were picked with a sterile toothpick and grown overnight at 37° C., 250 rpm in a 15 ml FALCON® tube containing 3 ml of LB medium supplemented with 100 μg of ampicillin per ml. The plasmids were isolated using the QIAGEN® robot protocol (QIAGEN, Valencia, Calif.).

Figure 3:
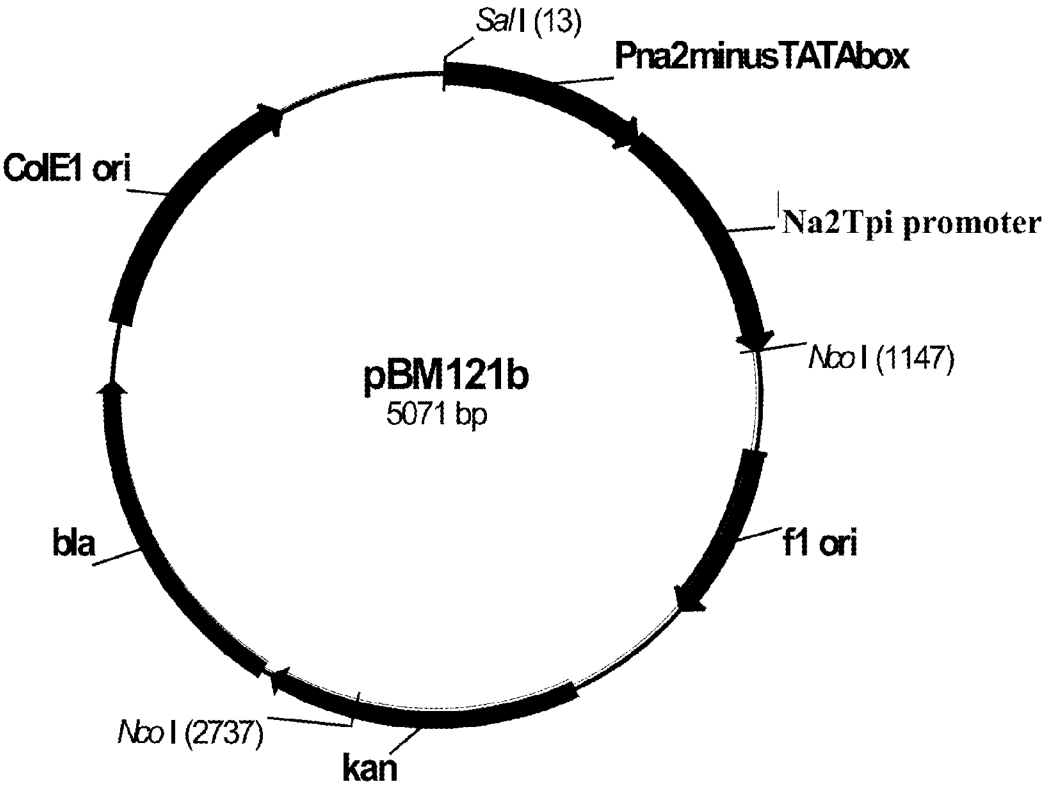
FIG. 3 shows a restriction map of pBM121b.

Four μl volumes of the resulting plasmid minipreps were digested with Eco RI. The digestion reactions were analyzed by agarose gel chromatography and UV analysis as previously described for the PCR reaction. Isolated plasmids containing an insert were sequenced using 1 μl of plasmid template, 1.6 ng of M13 primer (forward or reverse) (MWG Biotech; High Point; N.C.), and water to 6 μl. DNA sequencing was performed with an APPLIED BIOSYSTEMS® Model 377 Sequencer XL using dye-terminator chemistry. The resulting plasmid was designated pBM121b (FIG. 3).

Figure 4:
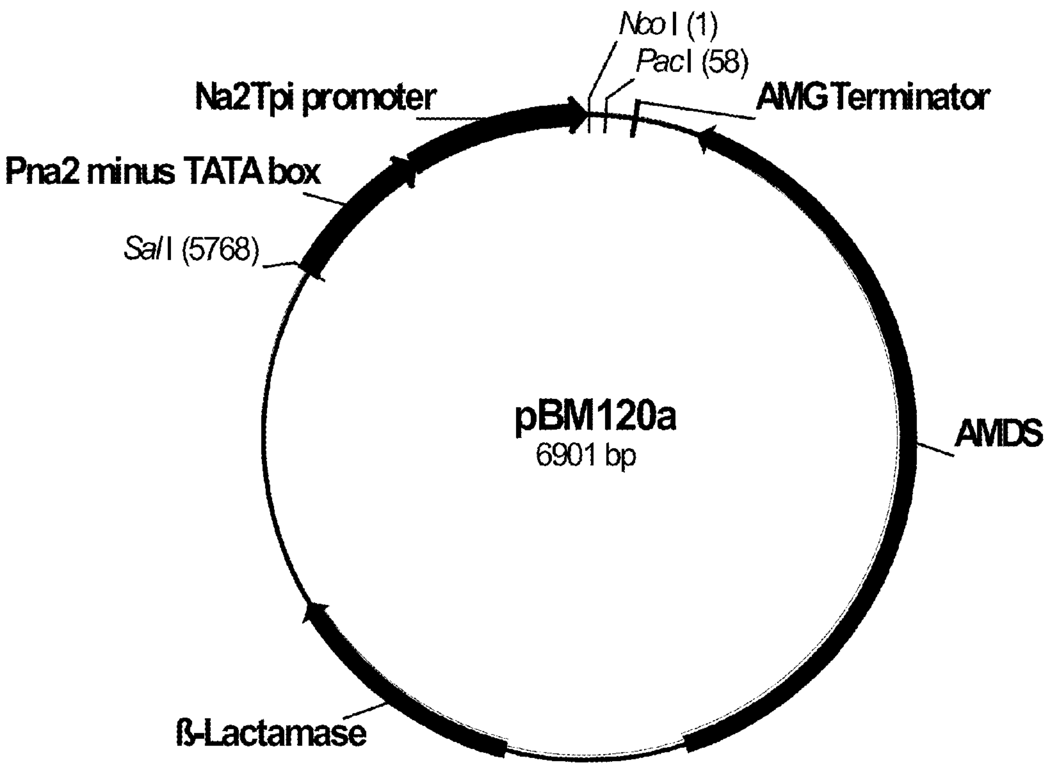

A 5 μl volume of pBM121b was digested with Sal I and Nco I. The digestion reactions were analyzed by agarose gel electrophoresis as described above, and ligated to the vector pAlLo1, which had been previously cleaved with Sal I and Nco I. The resulting expression plasmid was designated pBM120a (FIG. 4).

Example 5

Cloning of a Family GH10A Xylanase Gene and Construction of an *Aspergillus Oryzae* Expression Vector Two synthetic oligonucleotide primers shown below were designed to PCR amplify an *Aspergillus fumigatus* gene encoding a Family GH10A xylanase gene from the genomic DNA prepared in Example 2. An IN-FUSION® Cloning Kit (BD Biosciences, Palo Alto, Calif.) was used to clone the fragment directly into the expression vector pBM120a without the need for restriction digests and ligation.

Forward primer:
(SEQ ID NO: 16)
5'-TACACAACTGGCCATGCGTTTCTCCCTTGCCGC-3'

Reverse primer:
(SEQ ID NO: 17)
5'-AGTCACCTCTAGTTAATTAACTAGCATACAGTGCAGGGCT-3'

Bold letters represent coding sequence. The remaining sequence is homologous to insertion sites of pBM120a.

Fifty picomoles of each of the primers above were used in a PCR reaction containing 100 ng of *Aspergillus fumigatus* genomic DNA, 1× EXPAND® High Fidelity Amplification Buffer (Roche, Indianapolis, Ind.), 1.5 μl of a 10 mM blend of dATP, dTTP, dGTP, and dCTP, and 2.5 units of EXPAND® High Fidelity Polymerase (Roche, Indianapolis, Ind.), in a final volume of 50 μl. An EPPENDORF® MASTERCYCLER® thermocycler was used to amplify the fragment with the following settings: one cycle at 94° C. for 2 minutes; and 30 cycles each at 94° C. for 15 seconds, 60° C. for 30 seconds, and 70° C. for 3 minutes. The heat block then went to a 10° C. soak cycle.

The reaction products were isolated on a 1.0% agarose gel using TAE buffer where a 1.1 kb product band was excised from the gel and purified using a QIAQUICK® Gel Extraction Kit (QIAGEN, Valencia, Calif.) according to the manufacturer's instructions.

Figure 5:
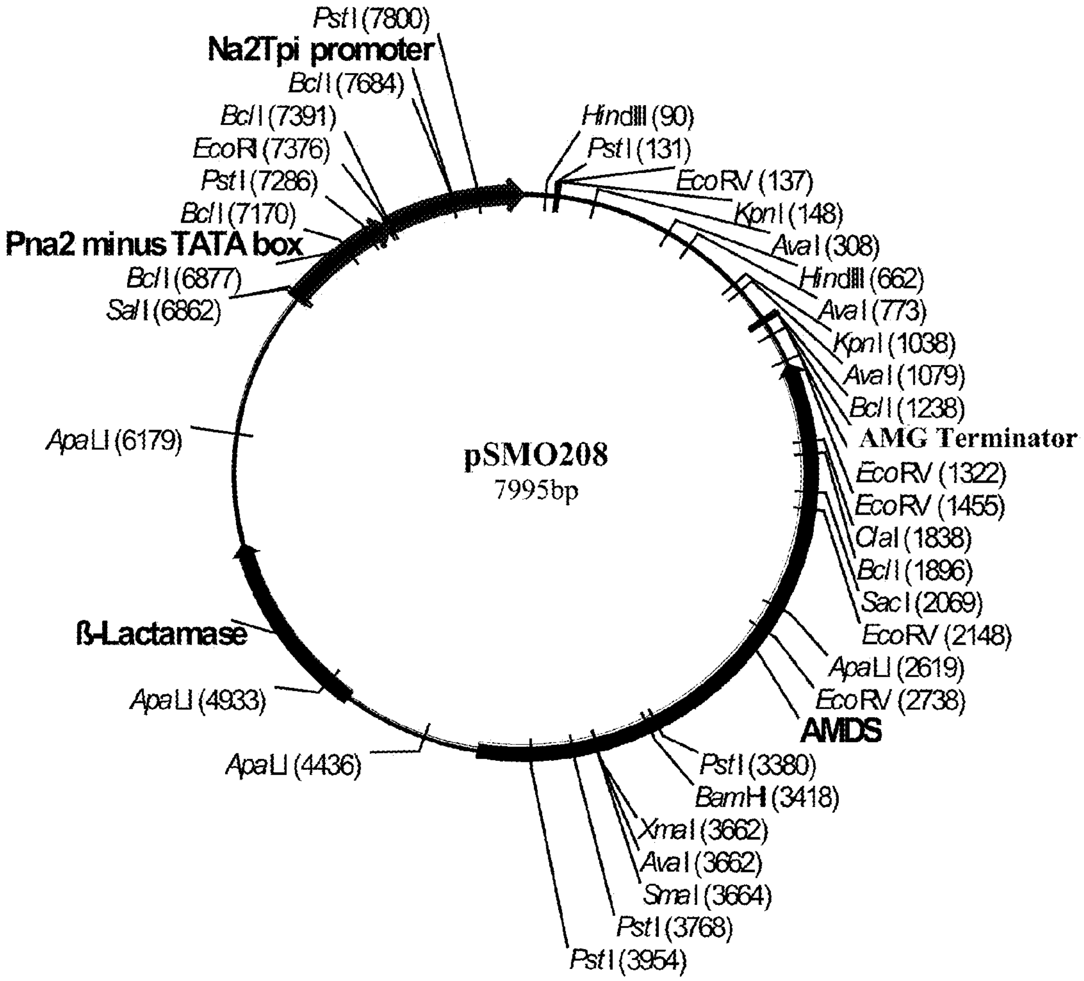
FIG. 5 shows a restriction map of pSMO208.

The fragment was then cloned into the expression vector pBM120a using an IN-FUSION® Cloning Kit. The vector was digested with Nco I and Pac I. The fragment was purified by agarose gel electrophoresis and QIAQUICK® gel purification as previously described. The gene fragment and digested vector were ligated together in a reaction resulting in the expression plasmid pSMO208 (FIG. 5) in which transcription of the Family GH10A xylanase gene was under the control of the NA2-NA2-tpi promoter. The ligation reaction (20 μl) was composed of 1× IN-FUSION® Buffer (BD Biosciences, Palo Alto, Calif.), 1× BSA (BD Biosciences, Palo Alto, Calif.), 1 μl of IN-FUSION® enzyme (diluted 1:10) (BD Biosciences, Palo Alto, Calif.), 100 ng of pBM120a digested with Nco I and Pac I, and 100 ng of the *Aspergillus fumigatus* xylanase purified PCR product. The reaction was incubated at room temperature for 30 minutes. One μl of the reaction was used to transform *E. coli* XL10 SOLOPACK® Gold cells (Stratagene, La Jolla, Calif.). An *E. coli* transformant containing pSMO208 was detected by restriction digestion and plasmid DNA was prepared using a BIOROBOT® 9600 (QIAGEN, Inc., Valencia, Calif.) according to the manufacturer's instructions.

Example 6

Characterization of the *Aspergillus Fumigatus* genomic Sequence Encoding a Family GH10A Xylanase DNA sequencing of the Family GH10A *Aspergillus fumigatus* xylanase gene from pSMO208 was performed with an APPLIED BIOSYSTEMS® Model 377 XL Automated DNA Sequencer (Perkin-Elmer/Applied Biosystems, Inc., Foster City, Calif.) using dye-terminator chemistry (Giesecke et al., 1992, *Journal of Virology Methods* 38: 47-60) and primer walking strategy. Nucleotide sequence data were scrutinized for quality and all sequences were compared to each other with assistance of PHRED/PHRAP software (University of Washington, Seattle, Wash.).

Sequence analysis of pSMO208 revealed 24 base-pair changes from the predicted sequence. Translation of the DNA sequence to amino acids resulted in 8 amino acid changes, including a stop codon at amino acid position 130. Site-directed mutagenesis was used to remove the stop codon and change one other amino acid to be more consistent with xylanase consensus sequences.

Example 7

Site-Directed Mutagenesis of the Family GH10A Xylanase Gene and Construction of an *Aspergillus Oryzae* Expression Vector To eliminate the stop codon at amino acid position 130, two synthetic oligonucleotide primers shown below were designed to PCR amplify the *Aspergillus fumigatus* GH10A xylanase gene containing a single by change using a QUIKCHANGE® IIXL Site-Directed Mutagenesis Kit (Stratagene, La Jolla, Calif.).

```
                                    (SEQ ID NO: 18)
5'-CCTCCAGGAACTGGACCGCCACAGAACTC-3'

                                    (SEQ ID NO: 19)
5'-GAGTTCTGTGGCGGTCCAGTTCCTGGAGG-3'
```

Fifty picomoles of each of the primers above were used in a PCR reaction containing 10 ng of pSMO208, 1× QUIKCHANGE® Amplification buffer (Stratagene, La Jolla, Calif.), 3 μl of QUIKCHANGE® Solution reagent, 1 μl of a 10 mM blend of dATP, dTTP, dGTP, and dCTP, and 2.5 units of EXPAND® High Fidelity Polymerase, in a final volume of 50 μl. An EPPENDORF® MASTERCYCLER® thermocycler was used to amplify the fragment with the following settings: one cycle at 95° C. for 2 minutes; 18 cycles each at 95° C. for 50 seconds, 60° C. for 50 seconds, and 68° C. for 8 minutes; and 1 cycle at 68° C. for 7 minutes. The heat block then went to a 10° C. soak cycle. Dpn I was added directly to the amplification reaction and incubated at 35° C. for 1 hour. A 2 μl volume of the Dpn I digested reaction was used to transform *E. coli* XL10 GOLD® Ultra competent cells. Plasmid DNA was prepared from an *E. coli* transformant using a BIOROBOT® 9600.

Sequence analysis verified the single base pair change removing the stop codon, resulting in pSMO209. To change the amino acid at amino acid position 169, two oligonucleotides were constructed as shown below.

997144:

```
                                          (SEQ ID NO: 20)
5'-GCTATTAATGGGGACGGGACCTTTTCCTCCAGTGTG-3'

997145:
                                          (SEQ ID NO: 21)
5'-CACACTGGAGGAAAAGGTCCCGTCCCCATTAATAGC-3'
```

Figure 6:
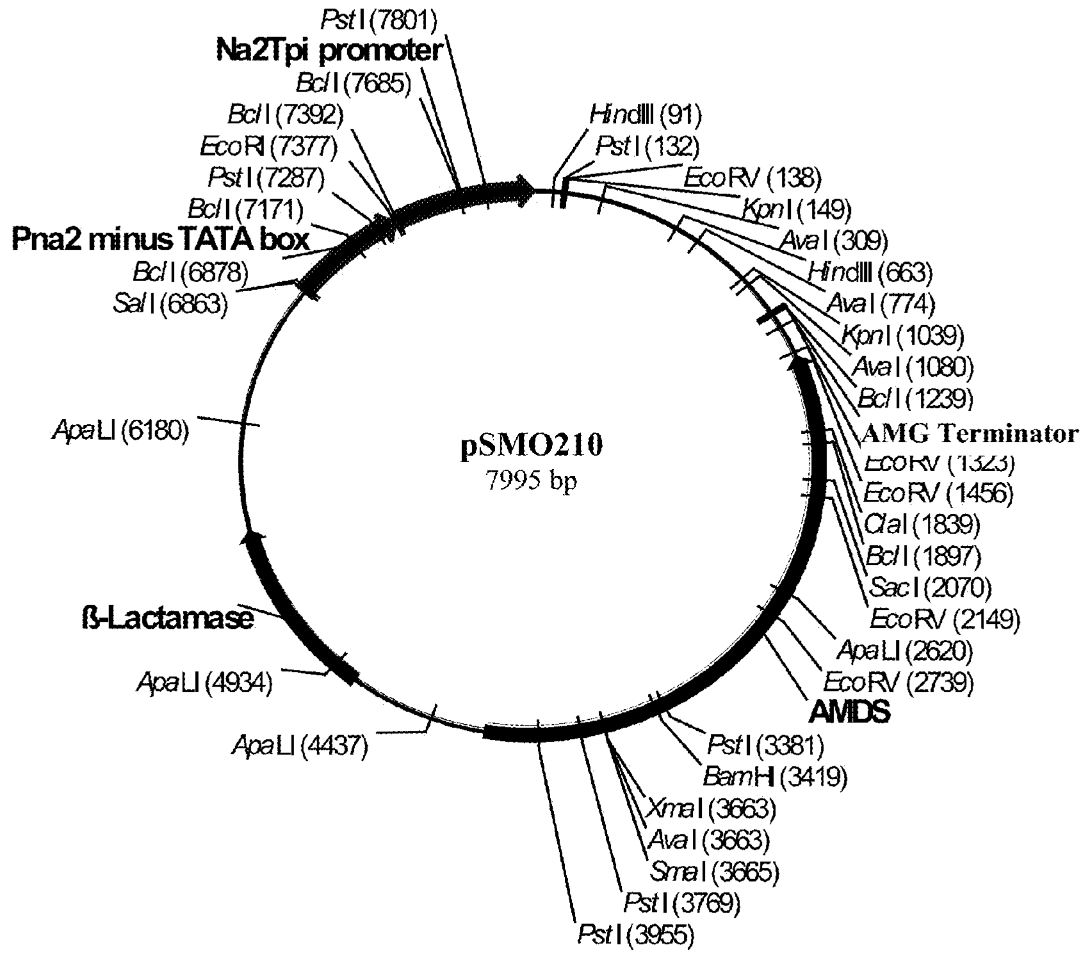
FIG. 6 shows a restriction map of pSMO210.

Fifty picomoles of each of the primers above were used in a PCR reaction containing 10 ng of pSMO209, 1× QUIKCHANGE® Amplification buffer, 3 μl of QUIKCHANGE® Solution reagent, 1 μl of a 10 mM blend of dATP, dTTP, dGTP, and dCTP, and 2.5 units of EXPAND® High Fidelity DNA Polymerase, in a final volume of 50 μl. An EPPENDORF® MASTERCYCLER® thermocycler was used to amplify the fragment with the following settings: one cycle at 95° C. for 2 minutes; 18 cycles each at 95° C. for 50 seconds, 60° C. for 50 seconds, and 68° C. for 8 minutes; and 1 cycle at 68° C. for 7 minutes. The heat block then went to a 10° C. soak cycle. Dpn I was directly added to the amplification reaction and incubated at 35° C. for 1 hour. A 2 μl volume of the Dpn I digested reaction was used to transform *E. coli* XL10 GOLD® Ultracompetent cells. Sequence analysis verified the base change resulting in pSMO210 (FIG. 6).

*E. coli* SoloPack Gold cells (Stratagene, La Jolla, Calif.) containing plasmid pSMO210 was deposited with the Agricultural Research Service Patent Culture Collection, Northern Regional Research Center, 1815 University Street, Peoria, Ill., 61604, as NRRL B-30706, with a deposit date of Feb. 6, 2004.

Example 8

Characterization of the *Aspergillus Fumigatus* Genomic Sequence Encoding a Family GH10A Xylanase DNA sequencing of the *Aspergillus fumigatus* GH10A xylanase gene from pSMO210 was performed with an APPLIED BIOSYSTEMS® Model 377 XL Automated DNA Sequencer (Perkin-Elmer/Applied Biosystems, Inc., Foster City, Calif.) using dye-terminator chemistry (Giesecke et al., 1992, supra) and primer walking strategy. Nucleotide sequence data were scrutinized for quality and all sequences were compared to each other with assistance of PHRED/PHRAP software.

A gene model for the Aspergillus fumigatus GH10A sequence of pSMO210 was constructed based on similarity to a homologous xylanase gene from *Myceliophthora thermophila* (accession number NP000134). The nucleotide sequence (SEQ ID NO: 1) and deduced amino acid sequence (SEQ ID NO: 2) are shown in FIGS. 1A and 1B. The genomic fragment encodes a polypeptide of 364 amino acids, interrupted by one 50 by intron. The % G+C content of the gene is 55.8%. Using the SignalP software program (Nielsen et al., 1997, *Protein Engineering* 10: 1-6), a signal peptide of 17 residues was predicted. The predicted mature protein contains 347 amino acids with a molecular mass of 40.4 kDa.

A comparative alignment of xylanase sequences was determined using the Clustal W method (Higgins, 1989, *CABIOS* 5: 151-153) using the LASERGENE® MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the Family GH10A *Aspergillus fumigatus* xylanase shares 36% identity to the deduced amino acid sequence of the *Myceliophthora thermophila* xylanase (Accession Number NP000134).

Example 9

Cloning of a Family GH10B Xylanase Gene and Construction of an *Aspergillus Oryzae* Expression Vector Two synthetic oligonucleotide primers shown below were designed to PCR amplify a *Aspergillus fumigatus* gene encoding a Family GH10B xylanase gene from the genomic DNA prepared in Example 2. An IN-FUSION® Cloning Kit was used to clone the fragment directly into the expression vector, pBM120a, without the need for restriction digests and ligation.

Forward primer:
(SEQ ID NO: 22)
5'-ACACAACTGGCCATGGTCGTCCTCAGCAAGCTCGTCA-3'

Reverse primer:
(SEQ ID NO: 23)
5'-AGTCACCTCTAGTTAATTAATCAGAGAGCAGCAATGATGG-3'

Bold letters represent coding sequence. The remaining sequence is homologous to the insertion sites of pBM120a.

The fragment of interest was amplified by PCR using the EXPAND® High Fidelity PCR System according to manufacturer's instructions. Each PCR reaction contained 250 ng of the genomic DNA template, 200 μM dATP, dTTP, dGTP, and dCTP mix, 1 μM forward and reverse primers, 1× reaction buffer, and 2.6 units of EXPAND® High Fidelity enzyme mix in a final volume of 50 μl. An EPPENDORF® MASTERCYCLER® thermocycler was used to amplify the fragment with the following settings: 1 cycle at 94° C. for 2 minutes; 10 cycles each at 94° C. for 15 seconds, 60° C. for 30 seconds, and 72° C. for 1.25 minutes; 15 cycles each at 94° C. for 15 seconds, 60° C. for 30 seconds, and 72° C. for 1.25 minutes plus 5 second elongation at each successive cycle; 1 cycle at 72° C. for 7 minutes; and a 10° C. hold.

The reaction products were isolated on a 0.7% agarose gel using 50 mM Tris base-50 mM boric acid-1 mM disodium EDTA (TBE) buffer and a 1.4 kb product band was excised from the gel and purified using a QIAQUICK® Gel Extraction Kit according to the manufacturer's instructions.

Figure 8:
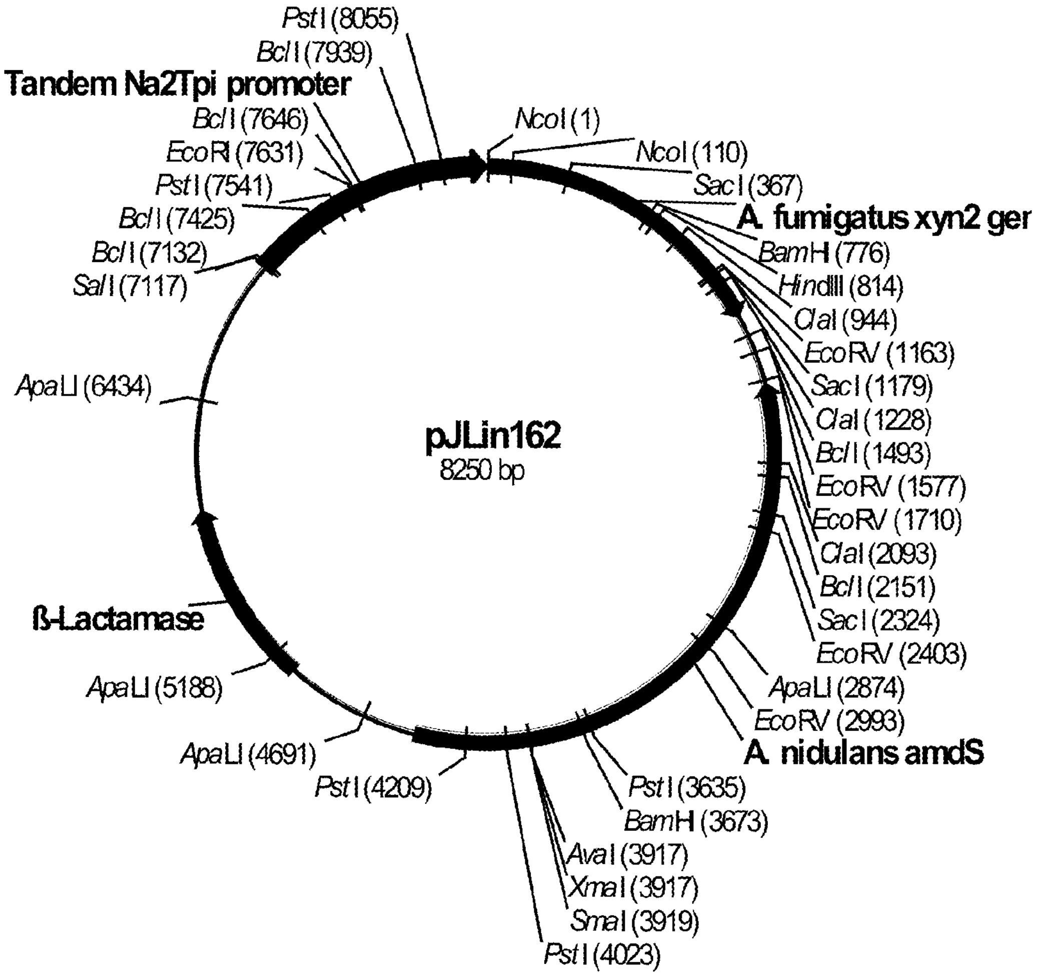
FIG. 8 shows a restriction map of pJLin162.

The fragment was then cloned into the expression vector pBM120a using an IN-FUSION® Cloning Kit. The vector was digested with Nco I and Pac I. Both the digested vector and PCR fragment were purified by gel electrophoresis and QIAQUICK® gel extraction as previously described. The gene fragment and digested vector were ligated together in a reaction resulting in the expression plasmid pJLin162 (FIG. 8) in which transcription of the Family GH10B xylanase gene was under the control of the NA2-NA2-tpi promoter. The ligation reaction (50 μl) was composed of 1× IN-FUSION® Buffer, 1× BSA, 1 μl of IN-FUSION® enzyme (diluted 1:10), 100 ng of pBM120a digested with Nco I and Pac I, and 50 ng of the *Aspergillus fumigatus* xylanase purified PCR product. The reaction was incubated at room temperature for 30 minutes. Two μl of the reaction was used to transform *E. coli* SOLOPACK® Gold supercompetent cells (Stratagene, La Jolla, Calif.). An *E. coli* transformant containing the pJLin162 plasmid was detected by restriction digestion and plasmid DNA was prepared using a BIOROBOT® 9600.

*E. coli* SOLOPACK® Gold cells containing plasmid pJLin162 were deposited with the Agricultural Research Service Patent Culture Collection, Northern Regional Research Center, 1815 University Street, Peoria, Ill., 61604, as NRRL B-30702, with a deposit date of Jan. 27, 2004.

Example 10

Characterization of the *Aspergillus Fumigatus* Genomic Sequence Encoding a Family GH10B Xylanase DNA sequencing of the *Aspergillus fumigatus* GH10B xylanase gene from pJLin162 was performed with an APPLIED BIOSYSTEMS® Model 377 XL Automated DNA Sequencer using dye-terminator chemistry (Giesecke et al., 1992, supra) and primer walking strategy. Nucleotide sequence data were scrutinized for quality and all sequences were compared to each other with assistance of PHRED/PHRAP software.

A gene model for the sequence was constructed based on the tfasty output and alignment with an *Aspergillus oryzae* xynF1 (Accession number AB011212). A comparative alignment of amino acid sequences was determined using the MAFFT method with iterative refinement and default parameters (Katoh et al., 2002, *Nucleic Acids Research* 30: 3059). The nucleotide sequence (SEQ ID NO: 3) and deduced amino acid sequence (SEQ ID NO: 4) are shown in FIGS. 7A and 7B. The genomic fragment encodes a polypeptide of 323 amino acids, interrupted by 8 introns of 57, 51, 56, 52, 55, 58, 49 and 52 bp. The % G+C content of the gene is 55.5%. Using the SignalP software program (Nielsen et al., 1997, supra), a signal peptide of 19 residues was predicted. The predicted mature protein contains 304 amino acids with a molecular mass of 33 kDa.

A comparative alignment of xylanase sequences was determined using the Clustal W method (Higgins, 1989, supra) using the LASERGENE® MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Aspergillus fumigatus* GH1OB xylanase gene shares 74% identity to the deduced amino acid sequence of the *Aspergillus oryzae* xylanase xynFl (accession number AB011212).

Example 11

Expression of the *Aspergillus Fumigatus* Family GH10B Xylanase Gene in *Aspergillus Oryzae* BECh2

*Aspergillus oryzae* BECh2 protoplasts were prepared according to the method of Christensen et al., 1988, *Bio/Technology* 6: 1419-1422. Two μg of pJLin162, which was digested with Pme I to remove the ampicillin resistance gene, was used to transform *Aspergillus oryzae* BECh2.

The transformation of *Aspergillus oryzae* BECh2 with pJLin162 yielded about 300 transformants. Forty-two transformants were transferred to individual COVE plates. Plugs of the *Aspergillus oryzae* BECh2 transformants along with the parental strain (as a negative control) were transferred to Minimal medium plates (adjusted to pH 5) containing 0.1% AZCL-arabinoxylan substrate (Megazyme, Ireland), and incubated at 37° C. overnight. All 42 transformants formed blue zones around the plugs, indicating expression of xylanase activity. Spores of the 42 transformants were then streaked to new COVE plates, followed by picking single colonies the next day. Two single colonies were picked for each transformant. The spore-purified clones were tested on AZCL-arabinoxylan plates again, and one xylanase-positive clone per each transformant was spore-purified the second time as described above.

Spores of 34 of the 42 transformants were collected in 4 ml of 0.01% TWEEN® 20 and 200 μl of the spore suspension were inoculated separately into 25 ml of MY25 medium in 125 ml plastic shake flasks and incubated at 34° C., 250 rpm. Three, four, and five days after inoculation, culture supernatants were removed and assayed for xylanase activity.

Culture supernatants prepared as described above were subjected to assay for xylanase activity as described below. Briefly, 135 μl of assay buffer (400 mM sodium phosphate pH 6 buffer) were mixed with 135 μl of 0.4% AZCL-arabinoxylan in 0.02% TRITON® X-100 for each reaction (with a final concentration of 0.2% substrate in 0.01% TRITON® X-100 and 200 mM sodium phosphate buffer). Then 30 μl of the diluted supernatant samples were added. Dilutions of SHEARZYME® 500 L, a purified xylanase from Aspergillus aculeatus (obtained from Novozymes NS, Bagsvrd, Denmark), at 600 FXU (fungal xylanase unit) per ml were used as a standard. After high-speed (1400 rpm) mixing at 37° C. for 15 minutes in an EPPENDORF® Thermomixer (Brinkmann Instruments, NY), samples were placed on ice for 2 minutes before centrifugation for 2 minutes at 1510×g. After centrifugation, 150 μl samples of the supernatants were measured at 650 nm. Xylanase activities of the transformants were determined by plotting the $A_{650}$ value against the standard curve generated by SHEARZYME® 500 L. All of the transformants were found to express xylanase activity. SDS-PAGE (BIO-RAD® CRITERION® 10-20% SDS-PAGE) analysis of 0.5 μl of the supernatants showed a major band at approximately 30 kDa.

Example 12

Cloning of a Family GH10C Xylanase Gene and Construction of an *Aspergillus Oryzae* Expression Vector Two synthetic oligonucleotide primers shown below were designed to PCR amplify a *Aspergillus fumigatus* gene encoding a Family GH10C xylanase gene from the genomic DNA prepared in Example 2. Vector pCR®2.1-TOPO (Invitrogen, Carlsbad, Calif.) was used to amplify the gene PCR product. The fragment of the gene was released by digesting with Nco I and Pac I and then ligated to expression vector pBM120a using a Rapid DNA Ligation Kit (Boehringer Mannheim, Germany) resulting in the expression plasmid pHyGe001.

```
Forward primer:
                                    (SEQ ID NO: 24)
5'-CCATGGTCCATCTATCTTCATT-3'

Reverse primer:
                                    (SEQ ID NO: 25)
5'-TTAATTAATTACAGGCACTGTGAGTACC-3'
```

Bold letters represent coding sequence. The remaining sequence is added for cloning sites.

Fifty picomoles of each of the primers above were used in a PCR reaction containing 100 ng of *Aspergillus fumigatus* genomic DNA, 1× EXPAND® High Fidelity Amplification Buffer, 1.5 μl of a 10 mM blend of dATP, dTTP, dGTP, and dCTP, and 2.5 units of EXPAND® High Fidelity Polymerase, in a final volume of 50 μl. An EPPENDORF® MASTERCYCLER® thermocycler was used to amplify the fragment with the following settings: one cycle at 94° C. for 2 minutes; 10 cycles each at 94° C. for 15 seconds, 56.8° C. for 30 seconds, and 72° C. for 1 minute and 15 seconds; 15 cycles each at 94° C. for 15 seconds, 60° C. for 30 seconds, and 72° C. for 1 minute and 15 seconds plus 5 second elongation at each successive cycle; and 1 cycle at 72° C. for 7 minutes. The heat block then went to a 10° C. soak cycle.

The reaction products were isolated on a 1.0% agarose gel using TAE buffer where a 1.4 kb product band was excised from the gel and purified using a QIAQUICK® Gel Extraction Kit according to the manufacturer's instructions.

Figure 10:
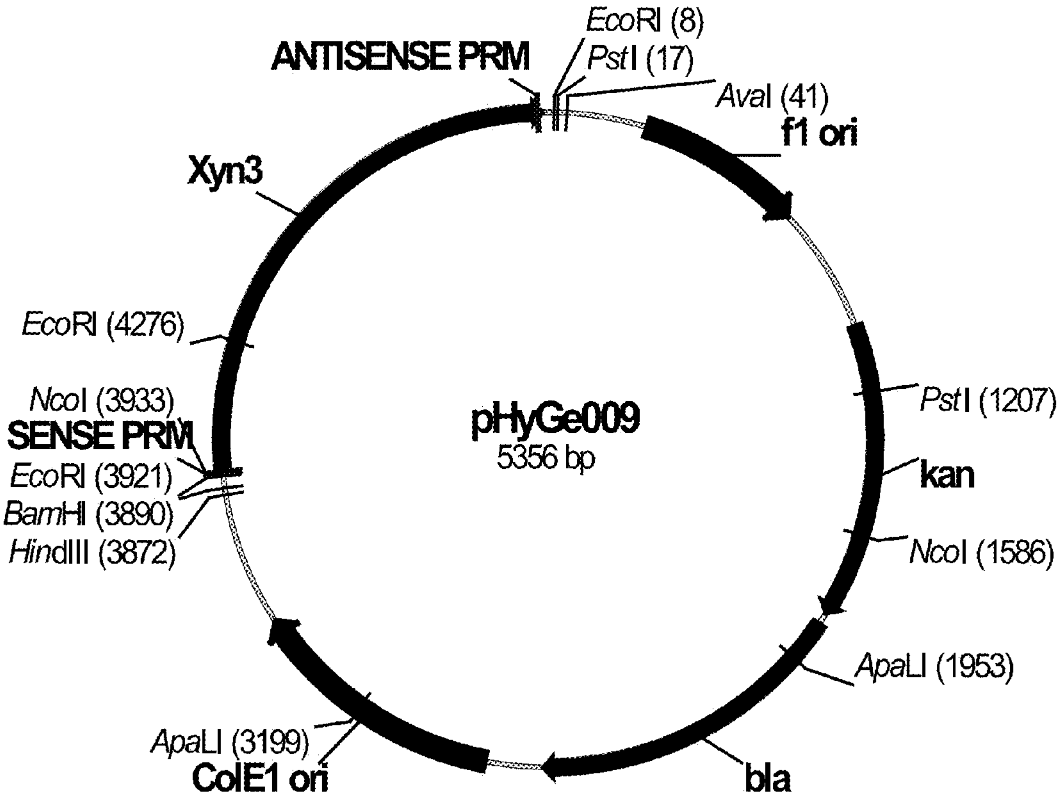
FIG. 10 shows a restriction map of pHyGe009.

The fragment was then cloned into the pCR2.1-TOPO vector. The gene fragment was purified by a PCR Clean Up Kit (QIAGEN, Valencia, Calif.). The fragment and pCR®2.1-TOPO vector were ligated by using conditions specified by the manufacturer resulting in plasmid pHyGe009 (FIG. 10). Two μl of the reaction was used to transform E. coli ONE SHOT® competent cells (Invitrogen, Carlsbad, Calif.). An *E. coli* transformant containing the plasmid pHyGe009 was detected by restriction digestion and plasmid DNA was prepared using a BIOROBOT® 9600.

Figure 11:
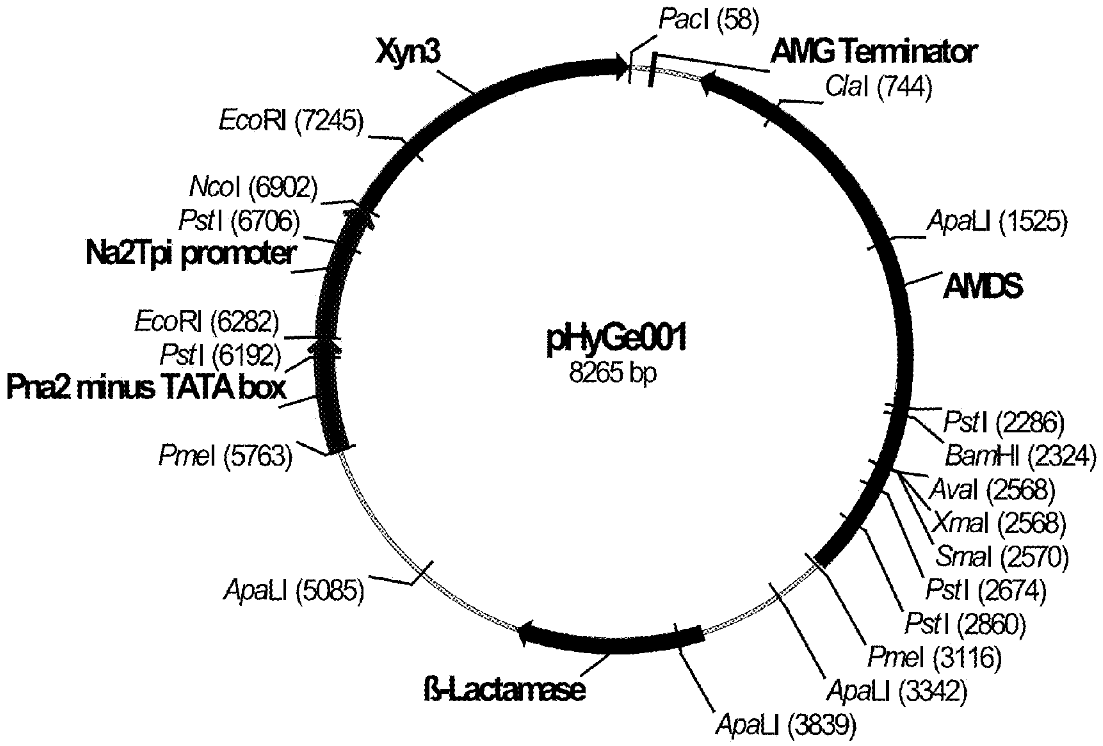
FIG. 11 shows a restriction map of pHyGe001.

The gene fragment from pHyGe009 was cloned into the pBM120a expression vector. The gene fragment was released from pHyGe009 by digestion with Nco I and Pac I and then purified by gel electrophoresis and QIAQUICK® gel purification as previously described. The pBM120a vector was digested with Nco I and Pac I. The gene fragment and the digested vector were ligated together using a Rapid DNA Ligation Kit resulting in expression plasmid pHyGe001 (FIG. 11) in which transcription of the Family GH10C xylanase gene was under the control of the NA2-NA2-tpi promoter. Five μl of the reaction was used to transform *E. coli* XL1-Blue Subcloning-Grade Competent Cells (Stratagene, La Jolla, Calif.). An *E. coli* transformant containing the pHyGe001 plasmid was detected by restriction digestion and plasmid DNA was prepared using a BIOROBOT® 9600.

*E. coli* TOP10 containing plasmid pHyGe001 was deposited with the Agricultural Research Service Patent Culture Collection, Northern Regional Research Center, 1815 University Street, Peoria, Ill., 61604, as NRRL B-30703, with a deposit date of Jan. 28, 2004.

Example 13

Characterization of the *Aspergillus Fumigatus* Genomic Sequence Encoding a Family GH10C Xylanase DNA sequencing of the *Aspergillus fumigatus* GH10C xylanase gene from pHyGe009 was performed with an APPLIED BIOSYSTEMS® Model 3700 Automated DNA Sequencer using dye-terminator chemistry (Giesecke et al., 1992, supra) and primer walking strategy. Nucleotide sequence data were scrutinized for quality and all sequences were compared to each other with assistance of PHRED/PHRAP software.

A gene model for the sequence was constructed based on the tfasty output and alignment with an *Aspergillus aculeatus* xylanase (Accession Number P48825). A comparative alignment of amino acid sequences was determined using the MAFFT method with iterative refinement and default parameters (Katoh et al., 2002, supra). The nucleotide sequence (SEQ ID NO: 5) and deduced amino acid sequence (SEQ ID NO: 6) are shown in FIGS. 9A and 9B. The genomic fragment encodes a polypeptide of 397 amino acids, interrupted by 4 introns of 49, 65, 48 and 59 bp. The % G+C content of the gene is 53%. Using the SignalP software program (Nielsen et al., 1997, supra), a signal peptide of 19 residues was predicted. The predicted mature protein contains 378 amino acids with a molecular mass of 40 kDa. A cellulose binding domain was identified using InterProScan software (Zdobnov, E. M. and Apweiler, R., 2001, InterProScan—an integration platform for the signature-recognition methods in InterPro, *Bioinformatics* 17(9): p. 847-8), which comprises 108 by from nucleotide 1305 to nucleotide 1412 encoding 36 amino acids with the deduced amino acid sequence of VAQKWGQCGGIGWTGPT-TCVSGTTCQKLNDWYSQCL (amino acids 362 to 397 of SEQ ID NO: 6).

A comparative alignment of xylanase sequences was determined using the Clustal W method (Higgins, 1989, supra) using the LASERGENE® MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the Aspergillus fumigatus GH10C xylanase gene shares 67.8% identity to the deduced amino acid sequence of the *Aspergillus aculeatus* xylanase (Accession Number P48825).

Example 14

Expression of the *Aspergillus Fumigatus* Family GH10C Xylanase Gene in *Aspergillus Oryzae* BECh2

*Aspergillus oryzae* BECh2 protoplasts were prepared according to the method of Christensen et al., 1988, supra. A 3.9 μg quantity of pHyGe001, which was digested with PmeI to remove the ampicillin resistance gene, was used to transform *Aspergillus oryzae* BECh2.

The transformation of *Aspergillus oryzae* BECh2 with pHyGe001 yielded about 49 transformants. The 49 transformants were transferred to individual COVE plates. Plugs of the *Aspergillus oryzae* BECh2 transformants along with the parental strain (as a negative control) were transferred to Minimal medium plates (adjusted to pH 6) containing 0.1% AZCL-arabinoxylan substrate (Megazyme, Ireland), and incubated at 37° C. overnight. Forty-one transformants formed blue zones around the plugs, indicating expression of xylanase activity. Spores of the 41 transformants were then streaked to new COVE plates, followed by picking single colonies the next day. Two single colonies were picked for each transformant. The spore-purified clones were tested on AZCL-arabinoxylan plates again, and one xylanase-positive clone per each transformant was spore-purified a second time as described above.

Spore stocks of the 41 of transformants were collected in 5 ml of 0.01% TWEEN® 20, and 200 pl of the spore suspension were inoculated into 25 ml of MY25 medium in 125 ml plastic shake flasks and incubated at 34° C., 250 rpm. Three, four, and five days after incubation, culture supernatants were removed and assayed for xylanase activity.

Culture supernatants prepared as described above were subjected to the xylanase assay as described in Example 11. The assay results demonstrated that all of the transformants expressed xylanase activity. SDS-PAGE (BIO-RAD® CRITERION® 10-20% SDS-PAGE) analysis of 10 μl of the supernatants showed a major band at approximately 50 kDa.

Deposit of Biological Materials

The following biological materials have been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| *E. coli* (pSMO210) | NRRL B-30706 | Feb. 6, 2004 |
| *E. coli* (pJLin162) | NRRL B-30702 | Jan. 27, 2004 |
| *E. coli* TOP10 (pHyGe009) | NRRL B-30703 | Jan. 28, 2004 |

The strains have been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposits represent a substantially pure culture of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A nucleic acid construct comprising an isolated polynucleotide encoding a polypeptide having xylanase activity operably linked to one or more heterologous control sequences that direct production of the polypeptide in a recombinant expression host, wherein the polynucleotide is selected from the group consisting of:

(a) a polynucleotide encoding a polypeptide having xylanase activity comprising an amino acid sequence having at least 95% identity to amino acids 20 to 323 of SEQ ID NO: 4;

(b) a polynucleotide encoding a polypeptide having xylanase activity which hybridizes under at least high stringency conditions with (i) nucleotides 58 to 1400 of SEQ ID NO: 3, (ii) the cDNA sequence of nucleotides 58 to 1400 of SEQ ID NO: 3, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes in 2×SSC, 0.2% SDS at 65° C.;

(c) a polynucleotide encoding a polypeptide having xylanase activity comprising a polynucleotide sequence having at least 95% identity to nucleotides 58 to 1400 of SEQ ID NO: 3;

(d) a polynucleotide encoding a polypeptide having xylanase activity comprising amino acids 20 to 323 of SEQ ID NO: 4; and (e) a polynucleotide encoding a polypeptide having xylanase activity comprising nucleotides 58 to 1400 of SEQ ID NO: 3.

2. The nucleic acid construct of claim 1, wherein the polynucleotide encodes a polypeptide having xylanase activity comprising an amino acid sequence having at least 95% identity to amino acids 20 to 323 of SEQ ID NO: 4.

3. The nucleic acid construct of claim 1, wherein the polynucleotide encodes a polypeptide having xylanase activity comprising an amino acid sequence having at least 97% identity to amino acids 20 to 323 of SEQ ID NO: 4.

4. The nucleic acid construct of claim 1, wherein the polynucleotide encodes a polypeptide having xylanase activity comprising the amino acid sequence of SEQ ID NO: 4, or a fragment thereof having xylanase activity.

5. The nucleic acid construct of claim 1, wherein the polynucleotide encodes a polypeptide having xylanase activity comprising the amino acid sequence of SEQ ID NO: 4.

6. The nucleic acid construct of claim 1, wherein the polynucleotide encodes a polypeptide having xylanase activity comprising amino acids 20 to 323 of SEQ ID NO: 4.

7. The nucleic acid construct of claim 1, wherein the polynucleotide hybridizes under at least high stringency conditions with (i) nucleotides 58 to 1400 of SEQ ID NO: 3, (ii) the cDNA sequence of nucleotides 58 to 1400 of SEQ ID NO: 3, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes in 2×SSC, 0.2% SDS at 65° C.

8. The nucleic acid construct of claim 7, wherein the polynucleotide hybridizes under at least very high stringency conditions with (i) nucleotides 58 to 1400 of SEQ ID NO: 3, (ii) the cDNA sequence of nucleotides 58 to 1400 of SEQ ID NO: 3, or (iii) the full-length complement of (i) or (ii), wherein very high stringency conditions are defined as prehybridization and hybridization at 42° C. in 5×SSPE, 0.3% SDS, 200 μg/ml sheared and denatured salmon sperm DNA, and 50% formamide and washing three times each for 15 minutes using 2×SSC, 0.2% SDS at 70° C.

9. The nucleic acid construct of claim 1, wherein the polynucleotide comprises a polynucleotide sequence having at least 95% identity to nucleotides 58 to 1400 of SEQ ID NO: 3.

10. The nucleic acid construct of claim 9, wherein the polynucleotide comprises a polynucleotide sequence having at least 97% identity to nucleotides 58 to 1400 of SEQ ID NO: 3.

11. The nucleic acid construct of claim 1, wherein the polynucleotide comprises SEQ ID NO: 3 or nucleotides 58 to 1400 of SEQ ID NO: 3.

12. The nucleic acid construct of claim 1, wherein the polynucleotide comprises the polynucleotide sequence contained in plasmid pJLin162 which is contained in *E. coli* NRRL B-30702.

13. A recombinant expression vector comprising the nucleic acid construct of claim 1.

14. An isolated recombinant host cell comprising the nucleic acid construct of claim 1.

15. A method for producing a polypeptide having xylanase activity comprising: (a) cultivating the recombinant host cell of claim 14 under conditions conducive for production of the polypeptide; and (b) recovering the polypeptide.

16. The nucleic acid construct of claim 1, wherein the polynucleotide is obtained by (a) hybridizing a population of DNA under at least high stringency conditions with (i) nucleotides 58 to 1400 of SEQ ID NO: 3, (ii) the cDNA sequence of nucleotides 58 to 1400 of SEQ ID NO: 3, or (iii) the full-length complementary strand of (i) or (ii); and (b) isolating the hybridizing polynucleotide, which encodes a polypeptide having xylanase activity, wherein high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes in 2×SSC, 0.2% SDS at 65° C.

17. The nucleic acid construct of claim 16, wherein the polynucleotide is obtained by (a) hybridizing a population of DNA under very high stringency conditions with (i) nucleotides 58 to 1400 of SEQ ID NO: 3, (ii) the cDNA sequence of nucleotides 58 to 1400 of SEQ ID NO: 3, or (iii) the full-length complementary strand of (i) or (ii); and (b) isolating the hybridizing polynucleotide, which encodes a polypeptide having xylanase activity, wherein very high stringency conditions are defined as prehybridization and hybridization at 42° C. in 5×SSPE, 0.3% SDS, 200 μg/ml sheared and denatured salmon sperm DNA, and 50% formamide and washing three times each for 15 minutes using 2×SSC, 0.2% SDS at 70° C.

18. A transgenic plant, plant part or plant cell, which has been transformed with the nucleic acid construct of claim 1.

19. A method for producing a polypeptide having xylanase activity, comprising: (a) cultivating the transgenic plant or the plant cell of claim 18 under conditions conducive for production of the polypeptide; and (b) recovering the polypeptide.

20. The nucleic acid construct of claim 1, wherein the polynucleotide encodes a polypeptide having xylanase activity comprising an amino acid sequence having at least 98% identity to amino acids 20 to 323 of SEQ ID NO: 4.

21. The nucleic acid construct of claim 1, wherein the polynucleotide encodes a polypeptide having xylanase activity comprising an amino acid sequence having at least 99% identity to amino acids 20 to 323 of SEQ ID NO: 4.

22. An isolated recombinant host cell transformed with a nucleic acid construct comprising an isolated polynucleotide encoding a polypeptide having xylanase activity operably linked to one or more control sequences that direct production of the polypeptide in the recombinant host cell, wherein the polypeptide having xylanase activity is heterologous to the recombinant host cell and wherein the polynucleotide is selected from the group consisting of:

(a) a polynucleotide encoding a polypeptide having xylanase activity comprising an amino acid sequence having at least 95% identity to amino acids 20 to 323 of SEQ ID NO: 4;

(b) a polynucleotide encoding a polypeptide having xylanase activity which hybridizes under at least high stringency conditions with (i) nucleotides 58 to 1400 of SEQ ID NO: 3, (ii) the cDNA sequence of nucleotides 58 to 1400 of SEQ ID NO: 3, or (iii) the full-length complement of (i) or (ii), wherein high stringency conditions are defined as prehybridization and hybridization at 42° C. in 5X SSPE, 0.3% SDS, 200 micrograms/ml sheared and denatured salmon sperm DNA, and 50% formamide, and washing three times each for 15 minutes in 2X SSC, 0.2% SDS at 65° C.;

(c) a polynucleotide encoding a polypeptide having xylanase activity comprising a polynucleotide sequence having at least 95% identity to nucleotides 58 to 1400 of SEQ ID NO: 3;

(d) a polynucleotide encoding a polypeptide having xylanase activity comprising amino acids 20 to 323 of SEQ ID NO: 4; and (e) a polynucleotide encoding a polypeptide having xylanase activity comprising nucleotides 58 to 1400 of SEQ ID NO: 3.

23. The recombinant host cell of claim 22, wherein the polynucleotide encodes a polypeptide having xylanase activity comprising an amino acid sequence having at least 95% identity to amino acids 20 to 323 of SEQ ID NO: 4.

24. The recombinant host cell of claim 22, wherein the polynucleotide encodes a polypeptide having xylanase activity comprising an amino acid sequence having at least 97% identity to amino acids 20 to 323 of SEQ ID NO: 4.

25. The recombinant host cell of claim 22, wherein the polynucleotide encodes a polypeptide having xylanase activity comprising an amino acid sequence having at least 98% identity to amino acids 20 to 323 of SEQ ID NO: 4.

26. The recombinant host cell of claim 22, wherein the polynucleotide encodes a polypeptide having xylanase activity comprising an amino acid sequence having at least 99% identity to amino acids 20 to 323 of SEQ ID NO: 4.

27. The recombinant host cell of claim 22, wherein the polynucleotide encodes a polypeptide having xylanase activity comprising the amino acid sequence of SEQ ID NO: 4, or a fragment thereof having xylanase activity.

28. The recombinant host cell of claim 22, wherein the polynucleotide encodes a polypeptide having xylanase activity comprising the amino acid sequence of SEQ ID NO: 4.

29. The recombinant host cell of claim 22, wherein the polynucleotide encodes a polypeptide having xylanase activity comprising amino acids 20 to 323 of SEQ ID NO: 4.

30. A method for producing a polypeptide having xylanase activity comprising: (a) cultivating the recombinant host cell of claim 22 under conditions conducive for production of the polypeptide; and (b) recovering the polypeptide.

* * * * *